(12) United States Patent
 Ikeda et al.

(10) Patent No.: US 10,831,755 B2
(45) Date of Patent: Nov. 10, 2020

(54) DATA PROCESSING APPARATUS AND DATA PROCESSING METHOD

(71) Applicant: SEIKO EPSON CORPORATION, Tokyo (JP)

(72) Inventors: Akira Ikeda, Chino (JP); Ayae Sawado, Kai (JP)

(73) Assignee: SEIKO EPSON CORPORATION, Tokyo (JP)

( * ) Notice: Subject to any disclaimer, the term of this patent is extended or adjusted under 35 U.S.C. 154(b) by 366 days.

(21) Appl. No.: 15/718,632

(22) Filed: Sep. 28, 2017

(65) Prior Publication Data

US 2018/0113911 A1   Apr. 26, 2018

(30) Foreign Application Priority Data

Oct. 26, 2016   (JP) .................. 2016-209167

(51) Int. Cl.
  *G06F 16/2455*   (2019.01)
  *G06F 16/248*   (2019.01)
  (Continued)

(52) U.S. Cl.
  CPC ...... *G06F 16/24553* (2019.01); *A61B 5/7264* (2013.01); *G06F 16/248* (2019.01); *G06F 16/26* (2019.01); *G16H 40/63* (2018.01); *G16H 50/20* (2018.01); *G16H 50/30* (2018.01); *A41D 1/002* (2013.01); *A41D 13/1281* (2013.01); *A61B 5/0205* (2013.01); *A61B 5/02438* (2013.01);
  (Continued)

(58) Field of Classification Search
  CPC .... G06F 16/24553; G06F 1/163; G06F 16/26; G06F 16/248; G16H 50/30; G16H 50/20; G16H 40/63; A41D 1/002; A41D 13/1281; A61B 5/7264; A61B 5/4866; A61B 5/1118; A61B 5/0205; A61B 5/681; A61B 5/6898; A61B 5/6802; A61B 5/02438
  See application file for complete search history.

(56) References Cited

U.S. PATENT DOCUMENTS

2009/0141593 A1* 6/2009 Taha .................. G01D 7/02
                                                    368/10
2010/0268056 A1* 10/2010 Picard ................ A61B 5/0531
                                                    600/388
(Continued)

FOREIGN PATENT DOCUMENTS

| JP | 2014-160358 A | 9/2014 |
| JP | 2015-103019 A | 6/2015 |
| WO | 2011/070831 A1 | 6/2011 |

OTHER PUBLICATIONS

Prauzek et al., "Fuzzy Clustering Method for Large Metabolic Data Set by Statistical Approach" Cairo International Biomedical Engineering Conference, 2014 (Year: 2014).*

*Primary Examiner* — David T. Brooks
(74) *Attorney, Agent, or Firm* — Oliff PLC

(57) ABSTRACT

A data processing apparatus includes an arithmetic processing unit that executes a data aggregation step of aggregating N types (N≥3) of sampling time series data to acquire M types (M≥2 and N>M) of classification time series data, a classification step of classifying the M types of classification time series data into a plurality of clusters, and an appearance data generation step of generating time series appearance data for each cluster.

5 Claims, 26 Drawing Sheets

| BIOMETRIC INFORMATION | COEFFICIENT VECTOR VALUE | |
|---|---|---|
| | FIRST PRINCIPAL COMPONENT | SECOND PRINCIPAL COMPONENT |
| HEAT FLUX | $\alpha_{11} = 0.61$ | $\alpha_{21} = -0.10$ |
| WRIST TEMPERATURE | $\alpha_{12} = -0.10$ | $\alpha_{22} = 0.97$ |
| SpO2 | $\alpha_{13} = -0.45$ | $\alpha_{23} = -0.17$ |
| PULSE RATE | $\alpha_{14} = 0.64$ | $\alpha_{24} = 0.12$ |

(51) Int. Cl.
  *G16H 50/20* (2018.01)
  *G16H 40/63* (2018.01)
  *G06F 16/26* (2019.01)
  *G16H 50/30* (2018.01)
  *A61B 5/00* (2006.01)
  *A41D 1/00* (2018.01)
  *A41D 13/12* (2006.01)
  *A61B 5/024* (2006.01)
  *G06F 1/16* (2006.01)
  *A61B 5/11* (2006.01)
  *A61B 5/0205* (2006.01)

(52) U.S. Cl.
  CPC ........... *A61B 5/1118* (2013.01); *A61B 5/4866* (2013.01); *A61B 5/681* (2013.01); *A61B 5/6802* (2013.01); *A61B 5/6898* (2013.01); *G06F 1/163* (2013.01)

(56) References Cited

U.S. PATENT DOCUMENTS

| | | | | |
|---|---|---|---|---|
| 2012/0123232 A1* | 5/2012 | Najarian | ............ | A61B 5/0022 600/345 |
| 2012/0157858 A1* | 6/2012 | Thakur | ............... | A61B 5/0205 600/484 |
| 2012/0310050 A1* | 12/2012 | Osorio | ................. | A61B 5/1118 600/300 |
| 2012/0316932 A1* | 12/2012 | Rahman | ............... | A61B 5/1118 705/14.1 |
| 2013/0310660 A1* | 11/2013 | Zuckerman-Stark | ...... A61B 5/7264 600/301 |
| 2014/0195184 A1* | 7/2014 | Maeda | ................ | G01D 18/006 702/85 |
| 2014/0372175 A1* | 12/2014 | Jain | ....................... | H04W 76/12 705/7.31 |
| 2015/0205692 A1* | 7/2015 | Seto | ....................... | G06F 11/008 702/182 |
| 2015/0317446 A1* | 11/2015 | Ash | ........................ | G06F 3/048 705/2 |
| 2016/0055190 A1* | 2/2016 | Bar-Yam | ............. | G06F 16/2237 707/693 |
| 2016/0110478 A1* | 4/2016 | Aggour | .................. | G06F 17/40 707/755 |
| 2017/0147753 A1* | 5/2017 | Han | ........................ | G16H 50/50 |
| 2017/0206464 A1* | 7/2017 | Clayton | ................... | G06N 3/0454 |
| 2017/0273617 A1* | 9/2017 | Kaji | ....................... | A61B 5/6892 |
| 2018/0008204 A1* | 1/2018 | An | ......................... | G16H 50/30 |
| 2018/0096243 A1* | 4/2018 | Patil | ...................... | G06N 3/084 |

* cited by examiner

| TIME t | $S_1(t)$: HEAT FLUX [W/m²] | $S_2(t)$: WRIST TEMPERATURE [°C] | $S_3(t)$: SpO2 [%] | $S_4(t)$: PULSE RATE [bpm] |
|---|---|---|---|---|
| t1 | 224.87 | 35.50 | 97.57 | 68.70 |
| t2 | 215.65 | 35.50 | 96.96 | 65.82 |
| t3 | 219.32 | 35.60 | 96.72 | 64.15 |
| t4 | 214.67 | 35.58 | 96.78 | 68.23 |
| t5 | 204.30 | 35.46 | 96.64 | 67.70 |
| t6 | 225.87 | 35.54 | 96.92 | 65.55 |
| ⋮ | ⋮ | ⋮ | ⋮ | ⋮ |

FIG. 6

| BIOMETRIC INFORMATION | COEFFICIENT VECTOR VALUE ||
|---|---|---|
| | FIRST PRINCIPAL COMPONENT | SECOND PRINCIPAL COMPONENT |
| HEAT FLUX | $\alpha_{11}=0.61$ | $\alpha_{21}=-0.10$ |
| WRIST TEMPERATURE | $\alpha_{12}=-0.10$ | $\alpha_{22}=0.97$ |
| SpO2 | $\alpha_{13}=-0.45$ | $\alpha_{23}=-0.17$ |
| PULSE RATE | $\alpha_{14}=0.64$ | $\alpha_{24}=0.12$ |

FIG.13

| TIME t | c(t) |
|---|---|
| t1 | 1 |
| t2 | 1 |
| t3 | 2 |
| t4 | 5 |
| t5 | 1 |
| t6 | 2 |
| ⋮ | ⋮ |

FIG.16

| TIME t | c(t) | CLUSTER MEMBERSHIP DEGREE DATA $B_C(t)$ | | | | | |
|---|---|---|---|---|---|---|---|
| | | $B_1(t)$ | $B_2(t)$ | $B_3(t)$ | $B_4(t)$ | $B_5(t)$ | $B_6(t)$ |
| t1 | 1 | 1 | 0 | 0 | 0 | 0 | 0 |
| t2 | 1 | 1 | 0 | 0 | 0 | 0 | 0 |
| t3 | 2 | 0 | 1 | 0 | 0 | 0 | 0 |
| t4 | 5 | 0 | 0 | 0 | 0 | 1 | 0 |
| t5 | 1 | 1 | 0 | 0 | 0 | 0 | 0 |
| t6 | 2 | 0 | 1 | 0 | 0 | 0 | 0 |
| ⋮ | ⋮ | ⋮ | ⋮ | ⋮ | ⋮ | ⋮ | ⋮ |

FIG.17

| TIME t | $S_1(t)$: AGE | RESIDENTIAL PLACE COORDINATES (X,Y) | | $S_4(t)$: PURCHASE PRICE [YEN] |
|---|---|---|---|---|
| | | $S_2(t)$:X[km] | $S_3(t)$:Y[km] | |
| 10:00 | 42 | 0.38 | 9.46 | 6,300 |
| 10:05 | 38 | 1.27 | 7.19 | 8,600 |
| 10:10 | 45 | −0.53 | 10.19 | 8,000 |
| 10:15 | 35 | 2.49 | 0.22 | 2,500 |
| 10:20 | 51 | −0.78 | −2.90 | 4,500 |
| 10:25 | 42 | 1.52 | 4.97 | 9,600 |
| 10:30 | 31 | 5.28 | 11.33 | 5,000 |
| 10:35 | 35 | −4.98 | 2.32 | 2,600 |
| 10:40 | 45 | 0.00 | 8.30 | 7,500 |
| 10:45 | 62 | −1.80 | 3.12 | 15,000 |
| ⋮ | ⋮ | ⋮ | ⋮ | ⋮ |

FIG.36

| BIOMETRIC INFORMATION | COEFFICIENT VECTOR VALUE ||
|---|---|---|
| | FIRST PRINCIPAL COMPONENT | SECOND PRINCIPAL COMPONENT |
| AGE | $\alpha_{11}=0.71$ | $\alpha_{21}=0.02$ |
| X COORDINATE | $\alpha_{12}=-0.05$ | $\alpha_{22}=0.69$ |
| Y COORDINATE | $\alpha_{13}=0.06$ | $\alpha_{23}=0.73$ |
| PURCHASE PRICE | $\alpha_{14}=0.70$ | $\alpha_{24}=-0.04$ |

FIG.38

DATA PROCESSING APPARATUS AND DATA PROCESSING METHOD

BACKGROUND

1. Technical Field

The present invention relates to a data processing apparatus or the like which processes sampling time series data.

2. Related Art

In the related art, there is known a method of clustering time series data into a plurality of clusters to use the classification result for data analysis. For example, JP-A-2014-160358 discloses a method in which a document with time information is divided into words and clustered to find clusters having a semantic unity, a relationship between time series data separately acquired and each cluster is estimated by a regression analysis, and the time series data is decomposed into cluster components.

The technique of JP-A-2014-160358 decomposes one type of time series data and associates it with cluster which is found from data with different time information. Therefore, it is possible to decompose single time series data into components correlated with the appearance of a target event, by classifying data with time information into clusters correlated with the appearance of a specific event. However, in a case where a plurality of pieces of time series data correlate with appearance of a plurality of events, it is possible to obtain components correlated with the appearance of each event from individual time series data, and analyze the components separately, but it is difficult to analyze the appearance of each event by considering a plurality of pieces of time series data in a complex manner.

SUMMARY

An advantage of some aspects of the invention is to provide a technique for analyzing appearance of a plurality of events by considering a plurality of time series data in a complex manner.

A first aspect of the invention is directed to a data processing apparatus including an arithmetic processing unit that executes a data aggregation step of aggregating N types ($N \geq 3$) of sampling time series data to acquire M types (M and $N > M$) of classification time series data, a classification step of classifying the M types of classification time series data into a plurality of clusters, and an appearance data generation step of generating time series appearance data for each cluster.

As another aspect of the invention, the data processing apparatus may be configured as a data processing method including a data aggregation step of aggregating N types ($N \geq 3$) of sampling time series data to acquire M types ($M \geq 2$ and $N > M$) of classification time series data, a classification step of classifying the M types of classification time series data into a plurality of clusters, and an appearance data generation step of generating time series appearance data for each cluster.

According to the first aspect and the like of the invention, it is possible to aggregate N types ($N \geq 3$) of sampling time series data and acquire M types ($M \geq 2$ and $N > M$) of classification time series data. It is possible to generate appearance data for each cluster by classifying M types of classification time series data into a plurality of clusters. According to this, it becomes possible to analyze appearance of plural events represented by each cluster, by considering a plurality of time series data in a complex manner.

As a second aspect of the invention, the data processing apparatus according to the first aspect of the invention may be configured such that the data aggregation step includes aggregating the N types of sampling data into X types ($X \geq M$) of classification time series data and selecting the M types from the X types of classification time series data.

According to the second aspect of the invention, it is possible to aggregate N types of sampling data into X types ($X \geq M$) of classification time series data, and select M types from among them.

As a third aspect of the invention, the data processing apparatus according to the second aspect of the invention may be configured such that the data aggregation step is a step of executing principal component analysis or factor analysis of the N types of sampling data to execute the aggregation, and performing the selection based on a magnitude of variance of the classification time series data.

According to the third aspect of the invention, it is possible to execute principal component analysis or factor analysis of the N types of sampling data, and acquire M types of classification time series data based on the variance.

As a fourth aspect of the invention, the data processing apparatus according to any one of the first to third aspects of the invention may be configured such that the classification step includes plotting the M types of classification time series data in an M-dimensional space, and clustering the plots to classify the plots into the plurality of clusters.

According to the fourth aspect of the invention, it is possible to execute clustering by plotting the M types of classification time series data in an M-dimensional space, and classify the plots into the plurality of clusters.

As a fifth aspect of the invention, the data processing apparatus according to any one of the first to fourth aspects of the invention may be configured such that the appearance data generation step includes calculating an appearance probability for each calculation time by averaging the classification time series data belonging to the cluster with a predetermined time width while shifting the calculation time.

According to the fifth aspect of the invention, it is possible to calculate an appearance probability in time series of the classification time series data belonging to each cluster by averaging each classification time series data for cluster with a predetermined time width.

As a sixth aspect of the invention, the data processing apparatus according to any one of the first to fifth aspects of the invention may be configured such that the arithmetic processing unit executes a display control step of controlling display of the time series appearance data in a form of a dial with a time axis in a circumferential direction.

According to the sixth aspect of the invention, it is possible to control display of the time series appearance data in a form of a dial with a time axis in a circumferential direction.

As a seventh aspect of the invention, the data processing apparatus according to any one of the first to sixth aspects of the invention may be configured such that the sampling data includes biometric information of any one of a heat flux, a wrist temperature, an oxygen saturation level in arterial blood, and a pulse rate.

According to the seventh aspect of the invention, it is possible to aggregate N types of sampling data including biometric information of any one of a heat flux, a wrist temperature, an oxygen saturation level in arterial blood, and a pulse rate into M types of classification time series data, and generate appearance data for each classified cluster.

BRIEF DESCRIPTION OF THE DRAWINGS

The invention will be described with reference to the accompanying drawings, wherein like numbers reference like elements.

FIG. 6 is a diagram showing an example of each piece of biometric information $S_n(t)$ at a time t in a tabular form.

FIG. 13 is a diagram showing coefficient vector values $\alpha_{1n}$ and $\alpha_{2n}$ for determining the first principal component $Y_1(t)$ and the second principal component $Y_2(t)$ in the first embodiment.

FIG. 16 is a diagram showing time series cluster data c(t).

FIG. 17 is a diagram showing cluster membership degree data $B_c(t)$.

FIG. 36 is a diagram showing an example of purchaser information $S_n(t)$ for one day.

FIG. 38 is a diagram showing coefficient vector values $\alpha_{1n}$ and $\alpha_{2n}$ for determining the first principal component $Y_1(t)$ and the second principal component $Y_2(t)$ in the second embodiment.

DESCRIPTION OF EXEMPLARY EMBODIMENTS

Figure 1:
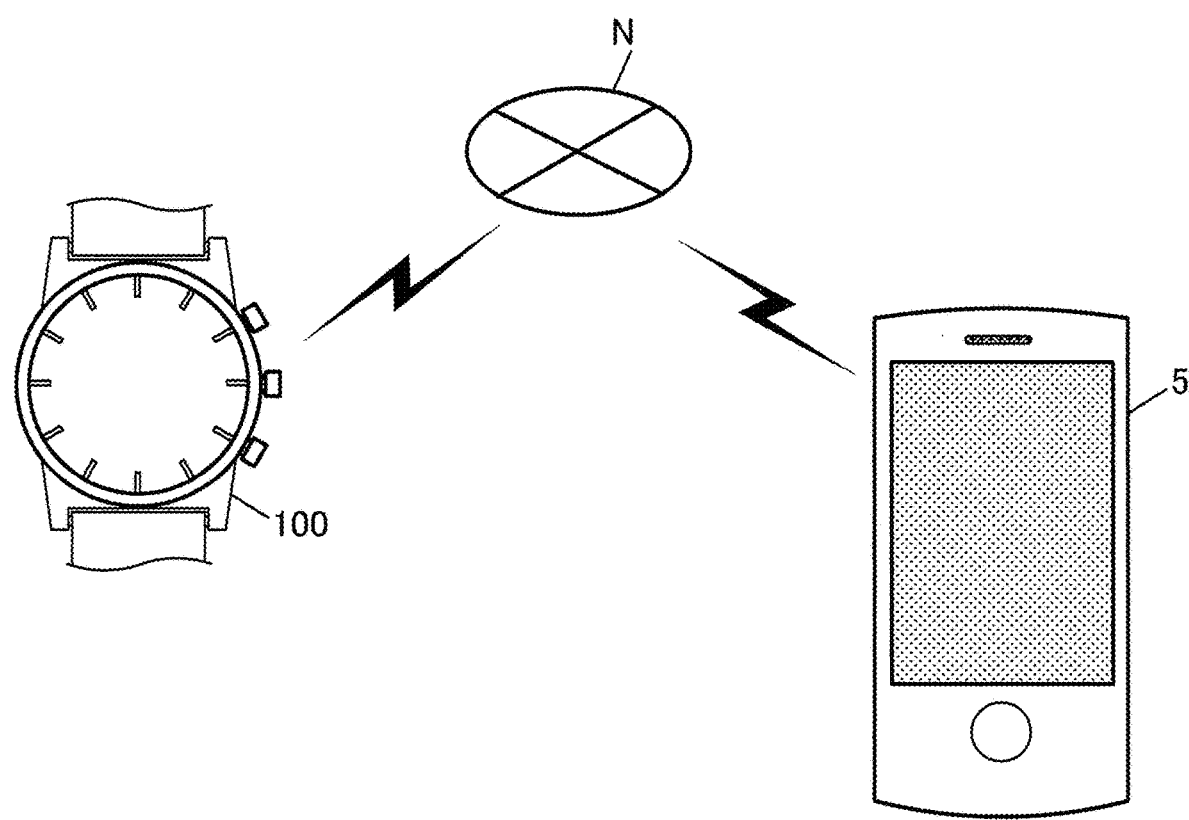
FIG. 1 is a schematic diagram showing a configuration example of an entire system including a data processing apparatus according to a first embodiment.

Hereinafter, preferred embodiments of the invention will be described with reference to the drawings. It should be noted that the invention is not limited by the embodiments to be described below, and aspects to which the invention can be applied are not limited to the following embodiments. In the description of the drawings, the same reference numerals are attached to the same parts.

First Embodiment

FIG. 1 is a schematic diagram showing a configuration example of an entire system including a data processing apparatus device 5 according to the first embodiment. The data processing apparatus 5 of the first embodiment is configured to be capable of data communication with a measuring apparatus 100 through a predetermined communication line N, and acquires biometric information of the user measured by the measuring apparatus 100 to perform analysis. The data processing apparatus 5 can be realized by using electronic devices such as a smartphone, a personal computer, a tablet computer, a mobile phone, a game device, or the like.

Figure 2:
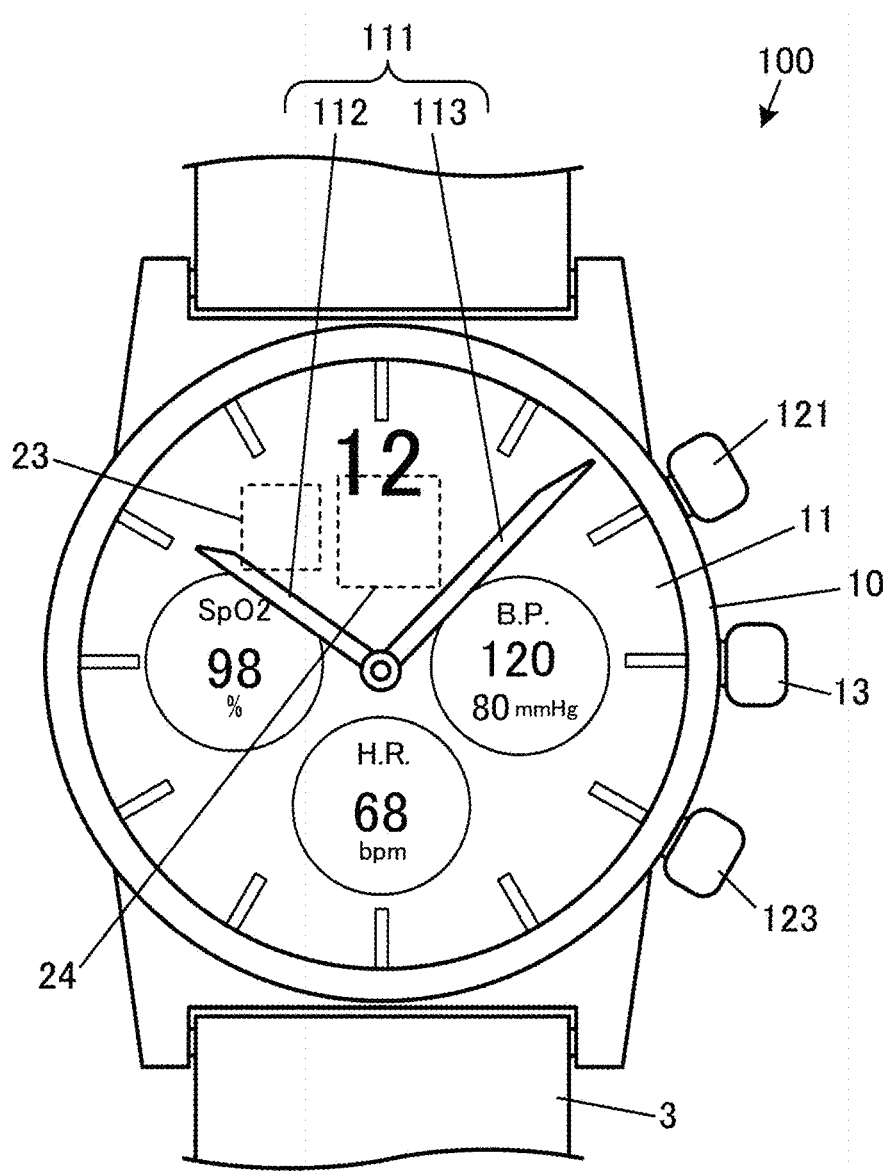
FIG. 2 is an external view of a measuring apparatus as seen from a front side.
Figure 3:
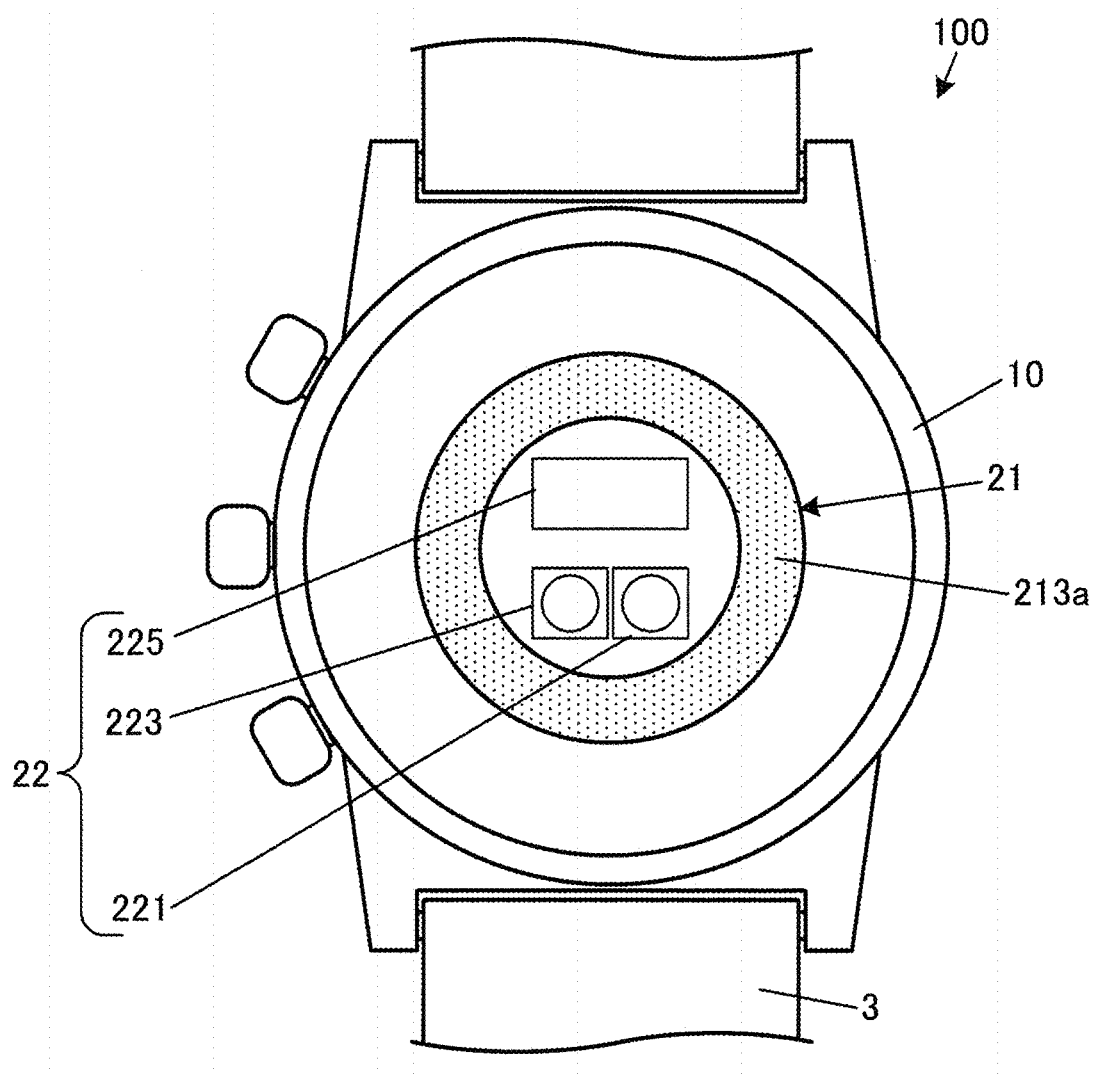
FIG. 3 is an external view of the measuring apparatus as seen from a back side.

FIGS. 2 and 3 are external views showing a configuration example of the measuring apparatus 100. FIG. 2 shows a front surface (a surface facing outward when worn by a user), and FIG. 3 shows aback surface (a surface contacting the user's skin when worn by the user). For example, the measuring apparatus 100 is configured as a wristwatch-type electronic device that displays the measured biometric information together with the current time, and the measuring apparatus 100 is attached and fixed on the biological surface (the skin surface of the wrist) by wrapping a band 3 provided on the main body case 10 around the user's wrist.

The measuring apparatus 100 is not limited to the configuration in which it is wrapped around the skin surface with the band 3, but may have a configuration in which it is attached to the skin surface of the user by using an adhesive sheet detachably attachable to the skin surface or a gel. Further, the measurement site on which the measuring apparatus 100 is mounted is not limited to the wrist. The measurement site may be appropriately selected, for example, from among a forehead, a neck, an upper arm, an ankle, a chest circumference, a waist circumference, a back of a hand or a foot, and the like.

The measuring apparatus 100 is provided with a dial 11 for displaying the current time, biometric information and the like, inside a main body case 10. On the outer peripheral portion of the main body case 10, operation switches 121 and 123 for inputting various operations such as start of measurement of biometric information and stop of the measurement, a crown 13 for manually adjusting the current time, and the like are disposed.

A pointer 111 for displaying the current time is disposed above the dial 11. In FIG. 2, the pointer 111 is illustrated as a two-needle type including an hour hand 112 and a minute hand 113, but it may be a three-needle type further having a second hand. The pointer 111 is driven and moved by a movement (not shown) provided on the rear side of the dial 11. Further, the dial 11 includes a display device such as a liquid crystal panel disposed on the front surface, and displays, for example, a blood pressure, an oxygen saturation level in arterial blood (SpO2), and a pulse rate (heart rate) measured as biometric information, individually. The display of the current time on the dial 11 is not limited to analog display but may be digital display. In addition, the type of biometric information to be displayed may be selected appropriately, and may be configured to be changeable according to the operation input by the user.

The measuring apparatus 100 includes a plurality of sensors arranged in place. For example, the measuring apparatus 100 incorporates a heat flow sensor 21, alight sensor 22, a motion sensor 23, and a GPS sensor 24. When a predetermined measurement start operation is performed, the measuring apparatus 100 continuously measures plural types of biometric information in parallel by these sensors 21 to 24, and transmits the measurement result to the data processing apparatus 5, at an appropriate timing such as a timing after a measurement end operation is performed. Measurement of each biometric information is performed at the same sampling time with a predetermined sampling period (for example, 1 [min]).

The heat flow sensor 21 measures the heat flow generated on the biological surface, based on the temperature difference generated inside the heat flow sensor 21 by the heat transfer between the biological surface of the measurement site (wrist in the present embodiment) to which the measuring apparatus 100 is attached and the outside environment. For example, the heat flow sensor 21 has a substantially annular shape in its outer shape, and a protective layer 213a forming one end surface thereof is disposed so as to be exposed on the back surface of the main body case 10.

Figure 4:
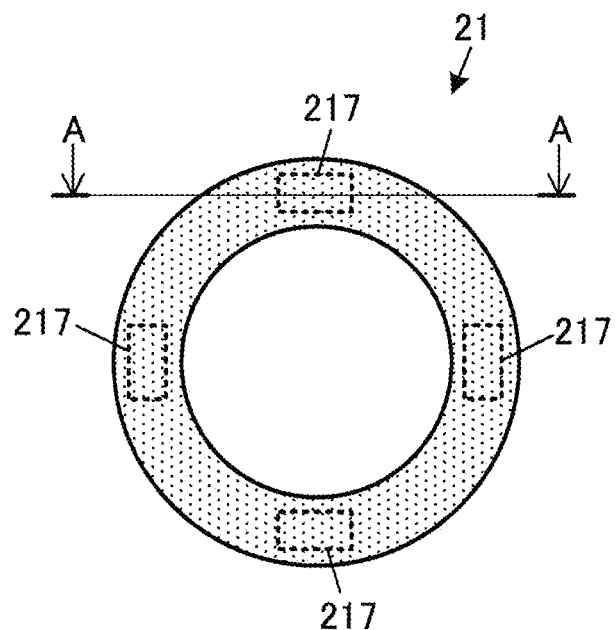
FIG. 4 is a plan view of a heat flow sensor.
Figure 5:
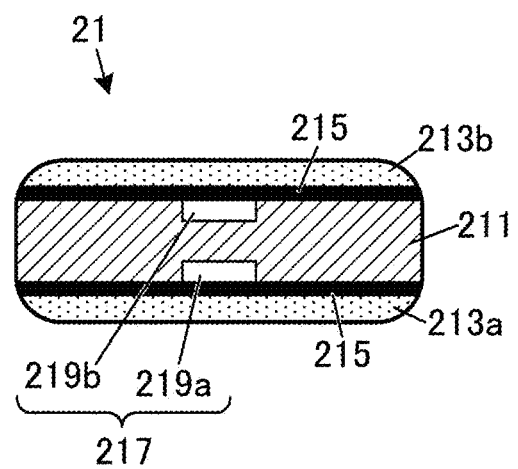
FIG. 5 is a schematic diagram of a cross section taken along line A-A shown in FIG. 4.
Figure 7:
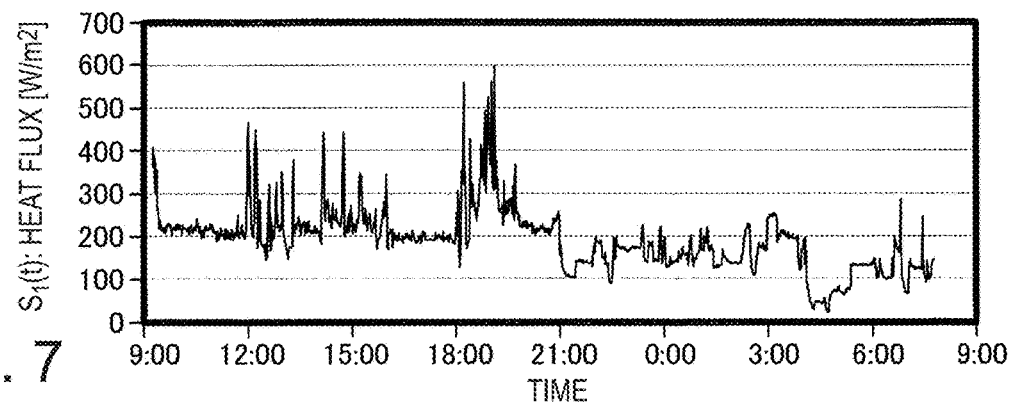
FIG. 7 is a graph showing a heat flux $S_1(t)$.
Figure 8:
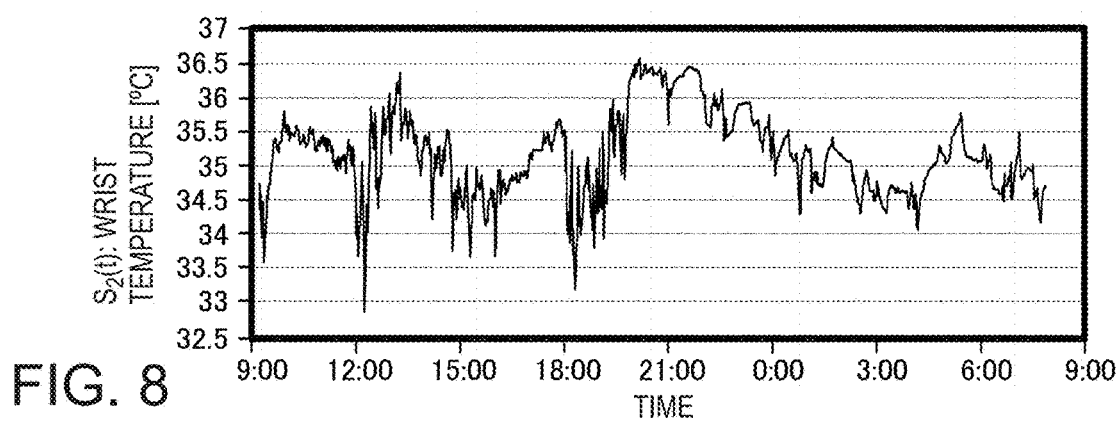
FIG. 8 is a graph showing a wrist temperature $S_2(t)$.
Figure 9:
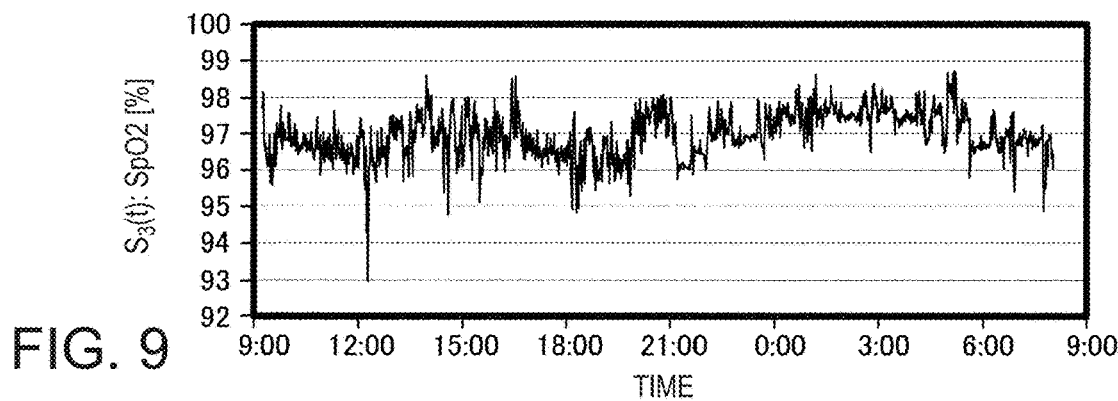
FIG. 9 is a graph showing an oxygen saturation level $S_3(t)$ in arterial blood.
Figure 10:
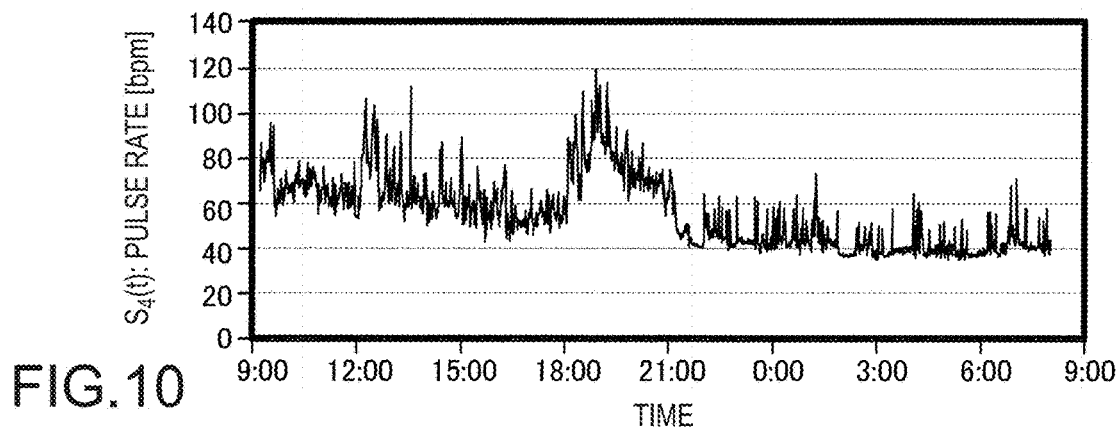
FIG. 10 is a graph showing a pulse rate $S_4(t)$.

FIG. 4 is a plan view of the heat flow sensor 21, and FIG. 5 is a schematic diagram of a cross section taken along line A-A shown in FIG. 4. The illustration of wirings and the like is omitted. As shown in FIGS. 4 and 5, the heat flow sensor 21 has a structure in which a heat transfer layer 211, the protective layer 213a covering the lower side in FIG. 5, and a protective layer 213b covering the upper side are mutually connected through a thermal diffusion layer 215, and includes a plurality of (four pieces in FIG. 4) detectors 217 are incorporated inside the heat transfer layer 211.

The detector 217 includes a temperature measuring body 219a disposed so as to be in contact with the protective layer 213a on the side of the biological surface at the time of mounting, and a temperature measuring body 219b disposed so as to be in contact with the protective layer 213b which is the outer environment side (the front side of the measuring apparatus 100) at a position facing the temperature measuring body 219a. The detected temperature of the temperature measuring body 219a is set as the skin temperature (wrist temperature) of the wrist, and the temperature detected by the temperature measuring body 219b is output as the heat transfer temperature. The heat flux (heat flow per unit area) at the position of the corresponding detector 217 can be measured from the temperature difference (vertical temperature difference) between temperatures detected by the temperature measuring bodies 219a and 219b. Further, from the wrist temperature and the heat flux, the deep portion temperature of the wrist can be measured by a relational expression based on the heat conduction equation. For the temperature measuring bodies 219a and 219b, a thermistor, a thermocouple or the like can be used. It should be noted that the configuration of the heat flow sensor 21 is not limited to the configuration using two temperature measuring bodies, and any known configuration such as one using a thermopile can be appropriately selected and used.

The light sensor 22 includes two light emitting units 221 and 223 disposed on the back surface of the main body case 10 such that the light emitting surfaces thereof are exposed, and a light receiving portion 225 disposed on the back surface of the main body case 10 such that the light receiving surface thereof is exposed, at the annular inner portion of the heat flow sensor 21. The light emitting surfaces of the light emitting units 221 and 223 and the light receiving surface of the light receiving portion 225 are protected by a transparent cover glass or the like covering the annular inner portion of the heat flow sensor 21.

The light emitting units 221 and 223 can be realized by using a light source such as an LED, an organic light emitting diode (OLED), and semiconductor laser which irradiates irradiation light within a predetermined wavelength range. The wavelength range of the irradiation light can be appropriately selected according to the measurement object. In the present embodiment, for example, one light emitting unit 221 irradiates visible light having a first wavelength in the vicinity of a wavelength region of 660 [nm], and the other light emitting unit 223 irradiates near infrared light having a second wavelength belonging to a wavelength region of 880 [nm] to 940 [nm].

The light receiving portion 225 receives the transmitted light and the reflected light of the irradiation light, and outputs a signal corresponding to the received light amount. For example, the light receiving portion 225 can be realized by a photodiode, a charge coupled device (CCD), a complementary metal oxide semiconductor (CMOS), or the like.

The light sensor 22 calculates a light receiving result by the light receiving unit 225 (the output value of the light receiving unit 225) with respect to irradiation light irradiated by one or both of the light emitting units 221 and 223 by using a known technique, and can measure biometric information such as a photoelectric pulse wave, a volume pulse wave, a pulse rate, a blood flow velocity, a blood flow rate, a blood perfusion amount, a blood vessel resistance, a blood pressure (diastolic blood pressure/systolic blood pressure), and an oxygen saturation level in arterial blood. Based on the output value of the light receiving unit 225 obtained by sequentially irradiating the irradiation light beams of the first wavelength and the second wavelength from the light emitting units 221 and 223, the oxygen saturation level in the arterial blood can be calculated from using the absorbance of the oxygenated hemoglobin and the reduced hemoglobin at each wavelength.

The heat flow sensor 21 and the light sensor 22 may be disposed such that the protective layer 213a of the heat flow sensor 21 and the portion of the cover glass that covers the light sensor 22 protrude from the back surface of the main body case 10 so as to easily come into contact with the biological surface when the measuring apparatus 100 is mounted. By improving the contact property, it is intended to prevent a decrease in measurement accuracy.

The motion sensor 23 is used for measuring the motion of the user and can be realized by, for example, a nine-axis sensor that detects acceleration (three axes), angular velocity (three axes), and geomagnetism (three axes). By calculating the output value of each of the acceleration, the angular velocity, and the geomagnetism of the motion sensor using a known technique, it is possible to measure information on the physical activity amount of the user, the number of steps, the moving distance, the speed, for example, posture such as "standing position", "sitting position", and "prison position", the types of exercise (motion) such as "walking", "running", and "stair climbing up and down".

The GPS sensor 24 is a sensor that receives a GPS satellite signal transmitted from a GPS satellite which is one type of positioning satellite and detects the position and the like of the user by using the received GPS satellite signal. In the present embodiment, the residential area of the user is set from the detection result of the GPS sensor 24. Since the method of detecting the position and the like of the user by using the GPS is well-known, the detailed explanation will be omitted.

It should be noted that the measuring apparatus 100 may further include a sensor for measuring the environmental information separately from the above-described sensor. For example, a temperature sensor, a humidity sensor, and an atmospheric pressure sensor may be provided. The temperature sensor can be realized by using, for example, a thermistor, a thermocouple, a platinum thermometer, or the like. As the humidity sensor, for example, a humidity sensor of a polymer resistor type, a polymer capacity type, an aluminum oxide capacity type or the like can be appropriately selected and used. As the barometric pressure sensor, a barometric pressure sensor of a MEMS electrostatic capacity type, a piezo-resistance type or the like can be appropriately selected and used.

Principle

In the first embodiment, four types of biometric information $S_n(t)$ (n=1 to 4) of heat flux $S_1(t)$ [W/m$^2$], wrist temperature $S_2(t)$ [° C.], oxygen saturation level in arterial blood $S_3(t)$ [%], and pulse rate $S_4(t)$ [bmp] which are measured every minute by the measuring apparatus 100 are used as N types (N≥3) of sampling time series data. FIG. 6 is a diagram showing an example of each piece of biometric information $S_n(t)$ at a time t ($t_1$, $t_2$, ...) in a tabular form. FIGS. 7 to 10 are graphs respectively showing the heat flux $S_1(t)$, the wrist temperature $S_2(t)$, the oxygen saturation level in arterial blood $S_3(t)$, and the pulse rate $S_4(t)$, with the horizontal axis as a time t.

In recent years, attempts to measure biometric information such as body temperature, blood pressure, and physical activity amount and utilize it for health management or the like are thriving. It is known that biometric information fluctuates depending on the condition of the living body, such as diet, exercise, breathing, sleeping, and the work of autonomic nerves (sympathetic nerves or parasympathetic nerves). For example, during exercise, generally the pulse rate and the heat flux rise. It is said that when parasympathetic nerves work, the pulse rate decreases and the wrist temperature rises. On the other hand, it is known that there is mutual relation among different types of biometric information. For example, as the pulse rate rises, the blood flow rate sent to the extremities rises, so the heat flux and the wrist temperature rise. Therefore, it is considered that the state of the living body can be analyzed by a method such as determining the threshold value of the biometric information whose correlation is known.

However, the relationship between the biometric information and the state of the living body is not completely formulated, and is merely an indication of the relationship as an aggregation of various experiment facts. There are also many cases where the relationship between biometric information is not clear, and it is difficult to clarify and formulate the mutual relationship between all types of biometric information. Therefore, in the analysis of the state of a certain living body from specific biometric information, it is failed to correctly recognize the state of the living body to be analyzed by being affected by the state of another living body or variation of biometric information in some cases.

Therefore, in the first embodiment, the state of the living body is analyzed, by (1) acquiring M types (M≥2 and N>M) of classification time series data by aggregating N types (four types in the first embodiment) of biometric information $S_n(t)$, (2) classifying the acquired classification time series data into clusters, and (3) generating time series appearance data for each of the classified clusters. The state analysis result of the living body is (4) displayed on the data processing apparatus 5, for example, and presented to the user.

(1) Data Aggregation Process

In the data aggregation process, firstly, the above-mentioned four types of biometric information $S_n(t)$ are normalized and used, and the principal component analysis of the biometric information $S_n(t)$ is performed. Principal component analysis can be performed using a known method, and coefficient vector value $\alpha_{Xn}$ for each type of normalized biometric information $S_n(t)$ can be obtained for each of the X types (X≥M) of principal components $Y_1(t)$ to $Y_X(t)$ orthogonal to each other. After performing the principal component analysis, M items are selected from the X types of principal components $Y_1(t)$ to $Y_X(t)$ to be M types of classification time series data. Hereinafter, M is set as 2, among the first principal component $Y_1(t)$ to the X-th principal component $Y_X(t)$, the first principal component $Y_1(t)$ having the largest variance $l_1(t)$ to $l_X(t)$ and the second principal component $Y_2(t)$ in the next order are selected to obtain two types of classification time series data. Through this process, the original four-dimensional information (heat flux, wrist temperature, oxygen saturation level in arterial blood, and pulse rate) is dimensionally compressed (aggregated) into two-dimensional information (first principal component and second principal component).

The normalization performed prior to the principal component analysis is not indispensable depending on the type of biometric information. For example, it is not necessary to normalize biometric information whose numerical values and fluctuation ranges are similar to each other such as blood pressure and pulse rate. Further, as a normalization method, a known method can be appropriately selected and used, and a separate method may be applied depending on the type of biometric information.

Figure 11:
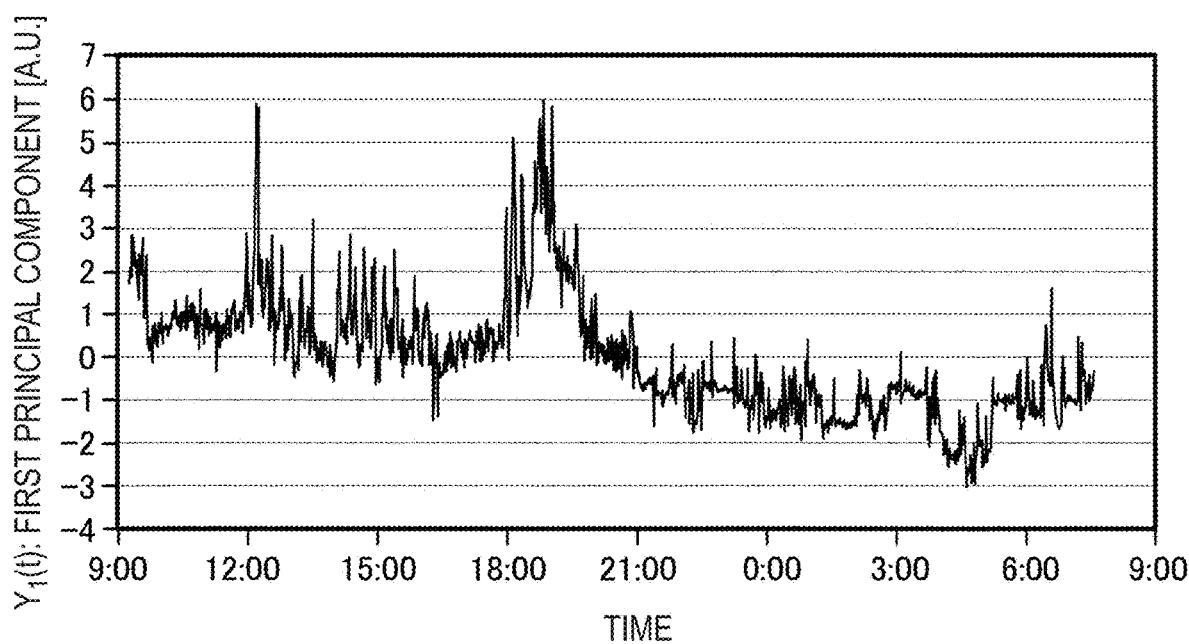
FIG. 11 is a graph showing a first principal component $Y_1(t)$ in the first embodiment.
Figure 12:
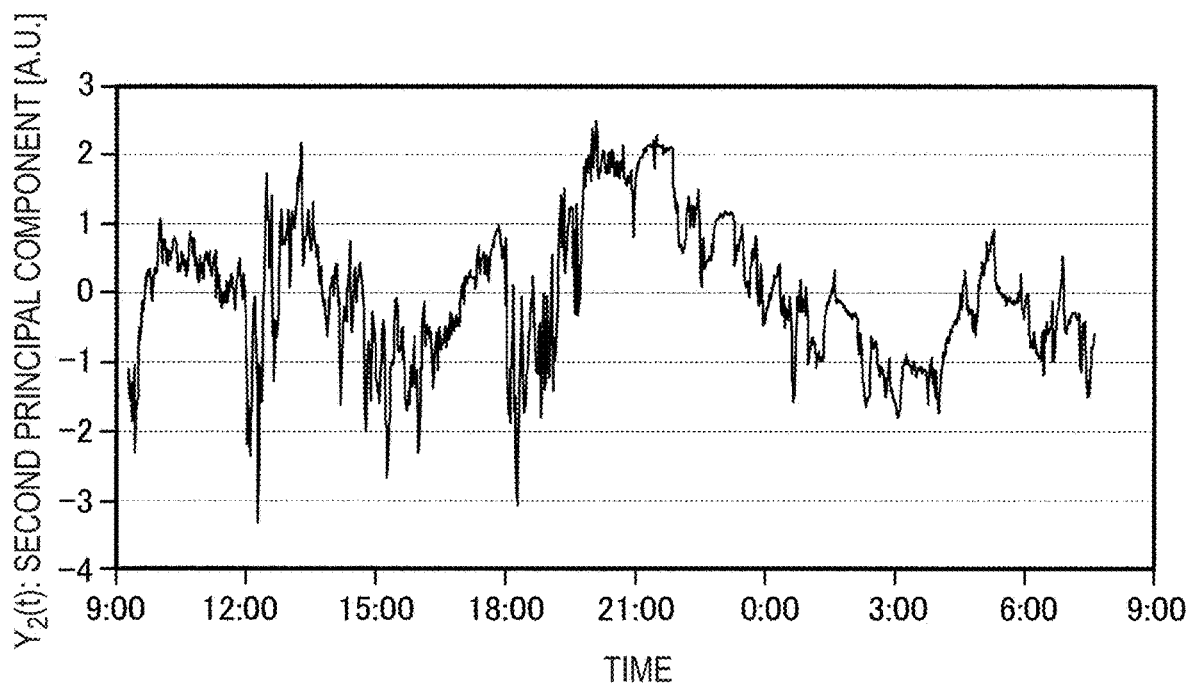
FIG. 12 is a graph showing a second principal component $Y_2(t)$ in the first embodiment.

FIG. 11 and FIG. 12 are diagrams showing the principal component analysis results of the biometric information $S_n(t)$ shown in FIGS. 6 to 10. FIGS. 11 and 12 are graphs respectively showing the first principal component $Y_1(t)$, and the second principal component $Y_2(t)$, with the horizontal axis as a time t. In addition, FIG. 13 shows a coefficient vector value $\alpha_{1n}$ associated with each piece of biometric information $S_n(t)$ defining the first principal component $Y_1(t)$ and a coefficient vector value $\alpha_{2n}$ associated with each piece of biometric information $S_n(t)$ defining the second principal component $Y_2(t)$.

Here, the first principal component $Y_1(t)$ is a linear sum obtained by multiplying each normalized biometric information $S_n(t)$ by a coefficient vector value $\alpha_{1n}$, and the second principal component $Y_2(t)$ is a linear sum obtained by multiplying each normalized biometric information $S_n(t)$ by a coefficient vector value $\alpha_{2n}$. That is, the coefficient vector value $\alpha_{1n}$ represents the degree of contribution (influence degree) of the corresponding biometric information $S_n(t)$ to the first principal component $Y_1(t)$, and the coefficient vector value $\alpha_{2n}$ represents the degree of contribution (influence degree) of the corresponding biometric information $S_n(t)$ to the second principal component $Y_2(t)$. Therefore, the meanings of the principal components $Y_1(t)$ and $Y_2(t)$ can be inferred from the values of the coefficient vector values $\alpha_{1n}$ and $\alpha_{2n}$.

First, in the first principal component $Y_1(t)$, as shown in FIG. 13, the coefficient vector value $\alpha_{11}$ for the heat flux and the coefficient vector value $\alpha_{14}$ for the pulse rate are large and are of the same positive value. The coefficient vector value $\alpha_{13}$ for the oxygen saturation level in the arterial blood is also relatively large and is a negative value. In general, since the heat flux means the amount of heat release, it is considered that there is a positive correlation with the basal metabolic rate. In addition, since the pulse rate has a positive correlation with the exercise intensity, it is considered that there is a positive correlation with the exercise metabolism rate. On the other hand, if the amount of metabolism increases due to exercise or the like, the amount of oxygen supplied from the arterial blood increases, so the oxygen saturation level in arterial blood is considered to decrease. Therefore, the first principal component $Y_1(t)$ can be interpreted as a measure representing the metabolic intensity.

Next, for the second principal component $Y_2(t)$, the coefficient vector value $\alpha_{22}$ related to the wrist temperature is large. In general, it is known that the temperature of the terminal part of the hand or the foot fluctuates due to the work of autonomic nerves. Therefore, the second principal component $Y_2(t)$ can be interpreted as a measure representing the degree of function of the autonomic nerve (whether it is a concentrated state dominated by sympathetic nerves or a relaxed state dominated by parasympathetic nerves).

As described above, according to the data aggregation process, the N types of biometric information are subjected to, for example, a principal component analysis to extract principal components and can be aggregated into M types of classification time series data (here, the metabolic intensity and the degree of automatic nervous function) useful for state analysis of a living body.

(2) Classification Process

Figure 14:
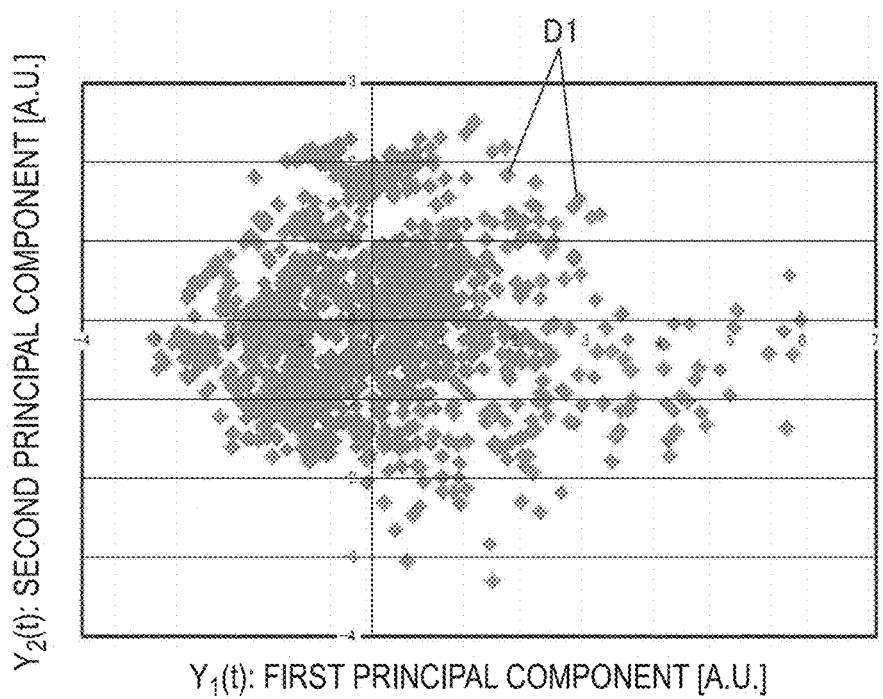
FIG. 14 is a diagram plotting aggregated data of the first principal component $Y_1(t)$ and the second principal component $Y_2(t)$ in the first embodiment.

In a classification processing, first, M types of classification time series data acquired by data aggregation process are plotted in an M-dimensional space. In the first embodiment, the first principal component $Y_1(t)$ and the second principal component $Y_2(t)$ which are acquired as the two types of classification time series data are formed into a pair at each time t ($t_1, t_2, \ldots$), and plotted in a two-dimensional space as aggregated data of each type of biometric information $S_n(t)$ measured at the corresponding a time t. FIG. 14 is a diagram plotting each aggregate data D1 with the horizontal axis representing the first principal component $Y_1(t)$ and the vertical axis representing the secondary principal component $Y_2(t)$. As described above, the first principal component $Y_1(t)$ represents metabolic intensity and the second principal component $Y_2(t)$ represents the degree of autonomic nervous function. Therefore, it is also possible to read, for example, the balance of momentum and autonomic nervousness, from the distribution of each aggregated data D1.

Figure 15:
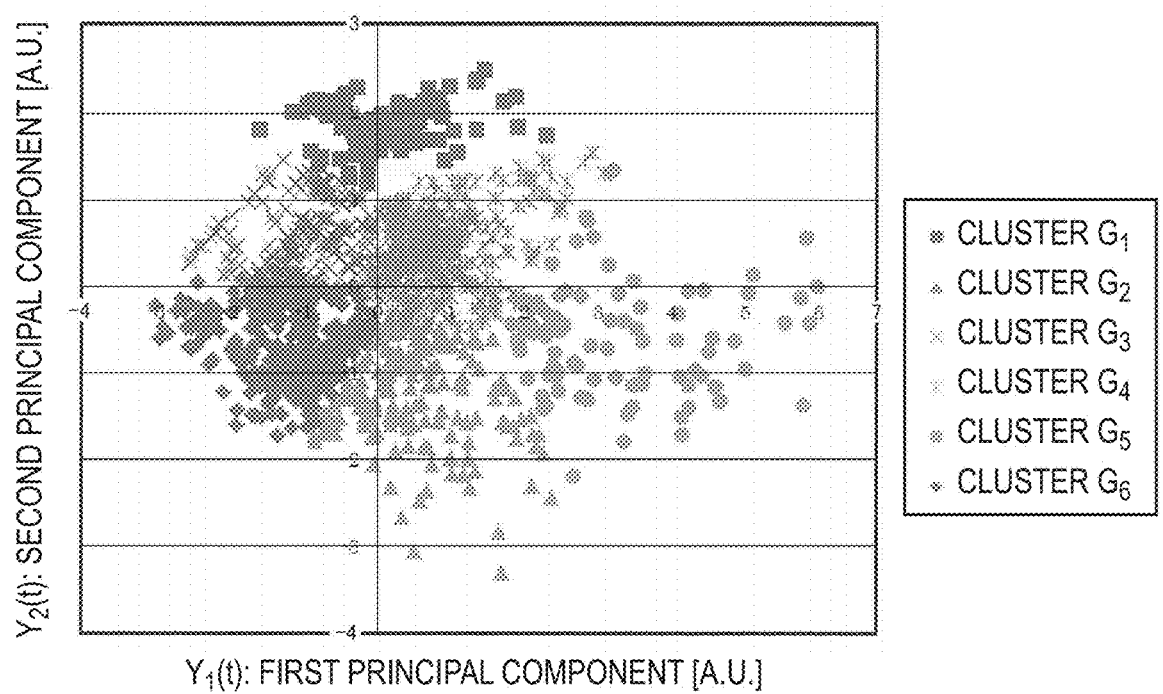
FIG. 15 is a diagram showing a clustering result of the aggregated data of FIG. 14.

Once the aggregated data is plotted, clustering is performed using a nonhierarchical clustering method, and each aggregated data is classified into s clusters. As the nonhierarchical clustering method, for example, a k-means method, a k-means++method, and the like are known, and a known method can be appropriately selected and used. FIG. 15 is a diagram showing the clustering result, and shows six clusters $G_1$ to $G_6$ obtained by classifying each aggregated data D1 of FIG. 14 by the k-means++method, with s=6. By the process here, each aggregated data D1 is divided into, for example, six groups, based on the distance between the aggregated data items D1 in the two-dimensional space.

(3) Appearance Data Generation Process

In the appearance data generation process, first, time series cluster data c(t) is generated based on the classification result of the cluster. FIG. 16 is a diagram showing time series cluster data c(t). As shown in FIG. 16, the time series cluster data c(t) is a data string in which the identification numbers c of the clusters to which each aggregated data D1 belongs are arranged in order of the time t ($t_1, t_2, \ldots$).

Subsequently, based on the time series cluster data c(t), a cluster membership degree data $B_c(t)$ (c=1, 2, ..., s) in time series determined for each of the clusters $G_1$ to $G_6$ as to whether or not the cluster to which each aggregated data D1 belongs is the own cluster. FIG. 17 is a diagram showing the cluster membership degree data $B_c(t)$ of each of the clusters $G_1$ to $G_6$, and also shows time series cluster data c(t) of FIG. 16. As shown in FIG. 17, the cluster membership degree data $B_c(t)$ is a data sequence in which the value of the time t associated with the aggregated data belonging to the corresponding cluster is "1" and the value of the other time t is "0". Therefore, focusing on a specific time t (see the table of FIG. 17 sideways), "1" is set to anyone of the cluster membership degree data $B_c(t)$. For example, focusing on the time t1, the cluster to which the aggregated data belongs is the cluster $G_1$ having the identification number c=1, from the time series cluster data c(t). Therefore, $B_1(t_1)$ is "1", and the other $B_2(t_1)$ to $B_6(t_1)$ is "0".

Assuming that each of the clusters $G_1$ to $G_6$ is related to some state of the living body, for example, it is possible to roughly know the state of the living body at the corresponding time t, depending on whether the value of $B_c(t)$ is "1" or "0". However, in reality, the state of the living body changes continuously, and it cannot be said that the binary value of "1" or "0" accurately reflects the state.

Therefore, when the cluster membership degree data $B_c(t)$ is generated, each cluster membership degree data $B_c(t)$ is sequentially processed, the appearance probability of the aggregated data is calculated for each calculation time, and an appearance data $P_c(t)$ of each of the cluster $G_1$ to $G_6$ is generated. Specifically, for example, each time t is used as the calculation time. Then, the average value of the cluster membership degree data $B_c(t)$ to be processed is calculated according to the following expression (1) with a predetermined time width based on the calculated time t. This is performed while shifting the calculation time t, and the calculated average value is used as the appearance probability at the corresponding time t of the aggregated data belonging to the cluster to obtain time series appearance data $P_c(t)$. The predetermined time width may be appropriately set, for example, to be 20 [min] before and after the calculation time t (that is, τ=10 [min]).

$$P_c(t) = \frac{1}{2\tau+1} \sum_{i=-\tau}^{\tau} B_c(t+i) \tag{1}$$

Figure 18:
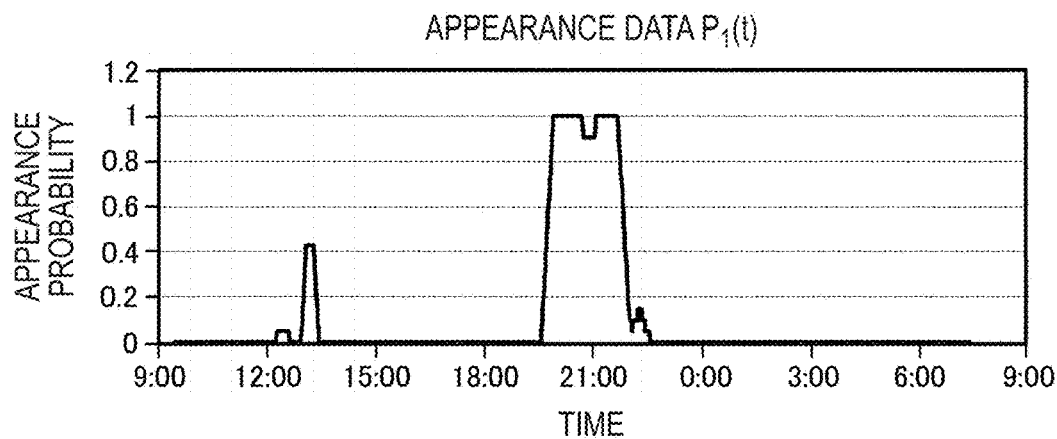
FIG. 18 is a graph of appearance data $P_1(t)$ of cluster $G_1$.
Figure 19:
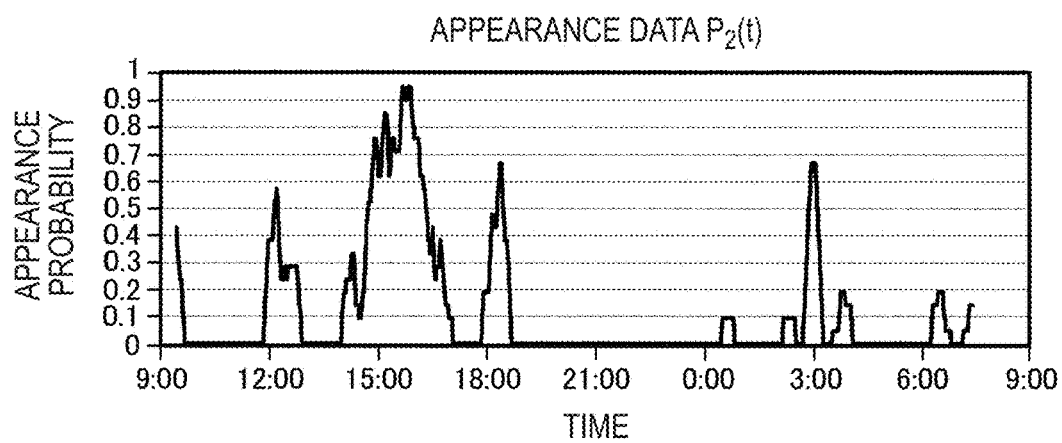
FIG. 19 is a graph of appearance data $P_2(t)$ of cluster $G_2$.
Figure 20:
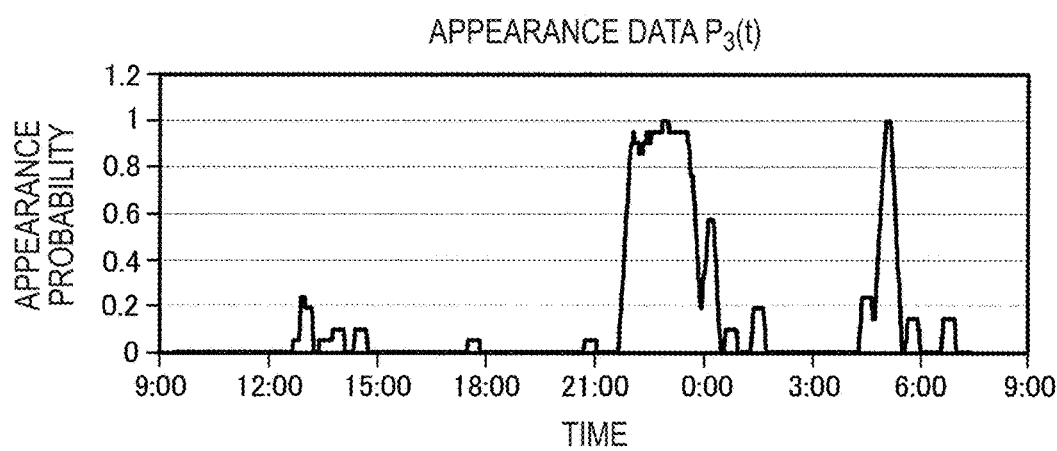
FIG. 20 is a graph of appearance data $P_3(t)$ of cluster $G_3$.
Figure 21:
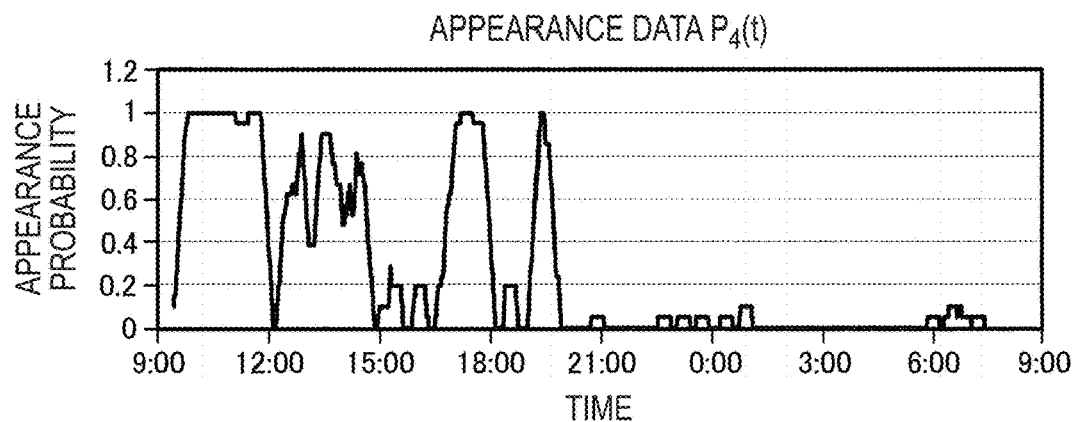
FIG. 21 is a graph of appearance data $P_4(t)$ of cluster $G_4$.
Figure 22:
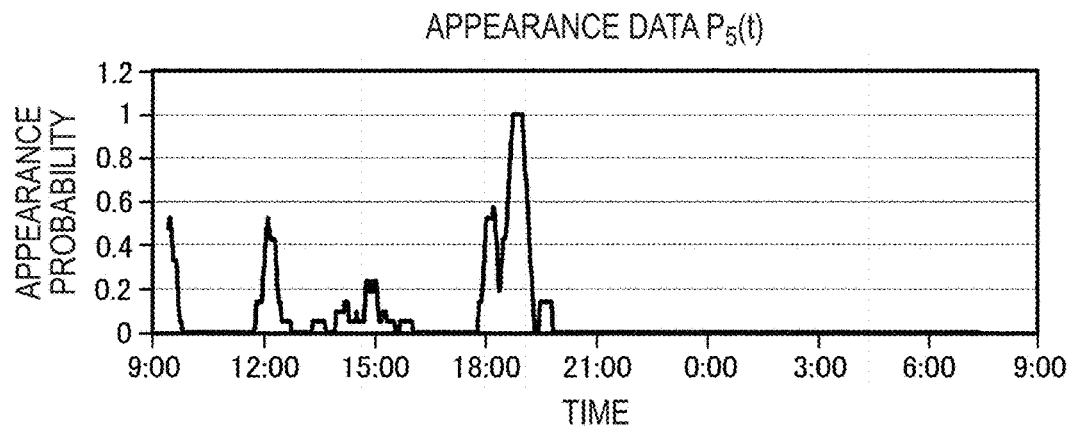
FIG. 22 is a graph of appearance data $P_5(t)$ of cluster $G_5$.
Figure 23:
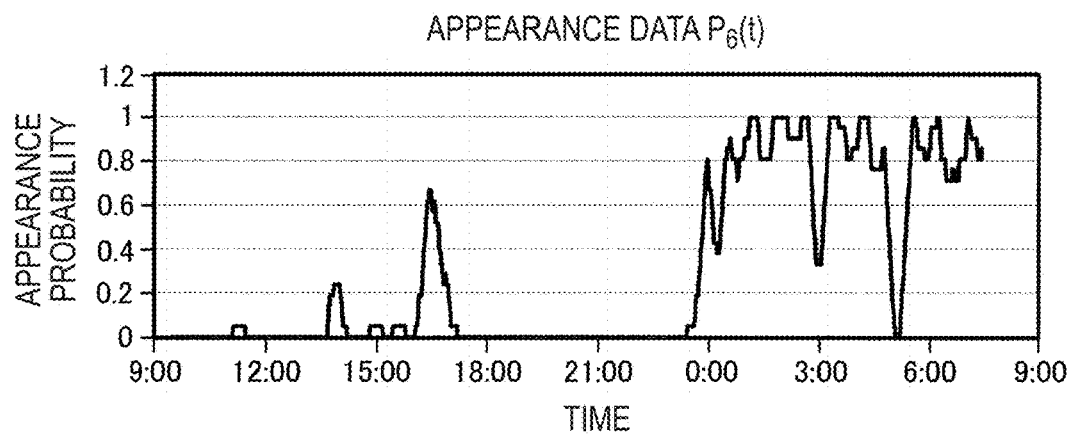
FIG. 23 is a graph of appearance data $P_6(t)$ of cluster $G_6$.

FIG. 18 shows a graph of the appearance data $P_1(t)$ of the cluster $G_1$, FIG. 19 shows a graph of the appearance data $P_2(t)$ of the cluster $G_2$, FIG. 20 shows a graph of the appearance data $P_3(t)$ of the cluster $G_3$, FIG. 21 shows a graph of the appearance data $P_4(t)$ of the cluster $G_4$, FIG. 22 shows a graph of the appearance data $P_5(t)$ of the cluster $G_5$, FIG. 23 shows a graph of the appearance data $P_6(t)$ of the cluster $G_6$, with the horizontal axis as the time t. According to FIG. 18 to FIG. 23, it can be seen that the aggregated data belonging to each of the clusters $G_1$ to $G_6$ is unevenly distributed temporally.

Figure 24:
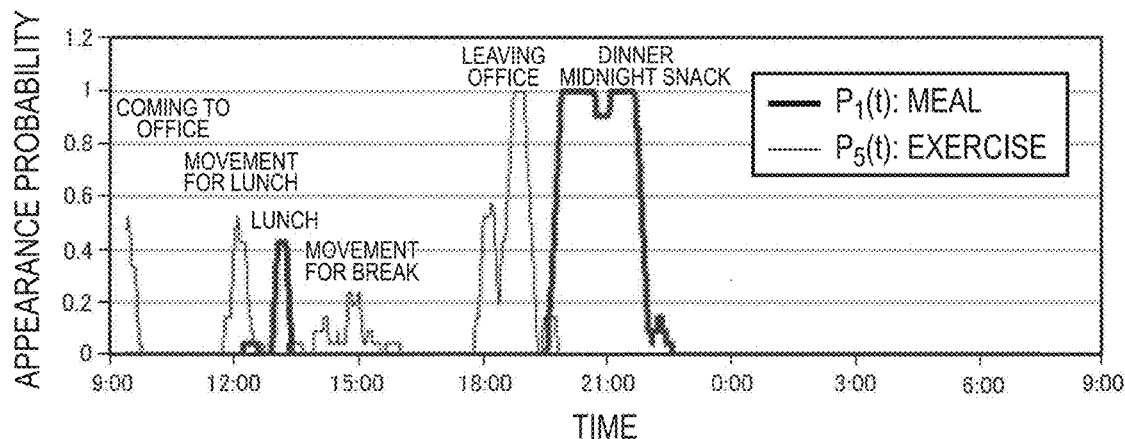
FIG. 24 is a graph obtained by overlapping the appearance data $P_1(t)$ and the appearance data $P_5(t)$.

Details will be described. First, attention is paid to the appearance data $P_1(t)$ and the appearance data $P_5(t)$. FIG. 24 is a graph obtained by overlapping the appearance data $P_1(t)$ and the appearance data $P_5(t)$ on a common time axis. According to the appearance data $P_1(t)$ and the appearance data $P_5(t)$, the aggregated data belonging to the cluster $G_1$ and $G_5$ appear around noon and appear from evening to night. Then, compared with the behavior of the user on the first day, the appearance time zone of the aggregated data related to the cluster $G_1$ coincides with the time zone of meal, and the appearance time zone of the aggregated data related to the cluster $G_5$ coincides with an exercise (walking) time zone when the user moves for commuting or meals. From this, it is considered that the appearance data P1 (t) represents the state of eating (meal state), and the appearance data P5 (t) represents the state of exercise (exercise state). As seen in FIG. 15, the cluster $G_5$ has a large metabolic intensity and is appropriate as a motion state.

Figure 25:
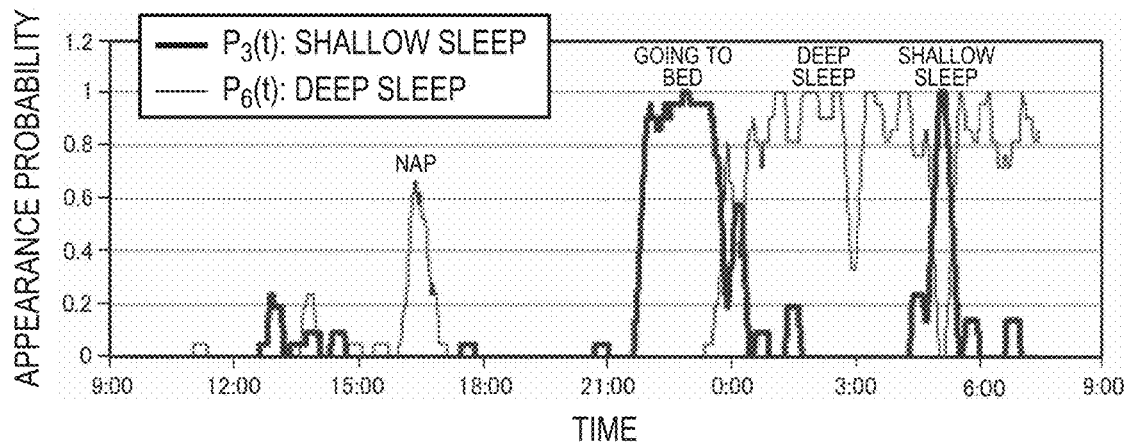
FIG. 25 is a graph obtained by overlapping the appearance data $P_3(t)$ and the appearance data $P_6(t)$.

Next, attention is paid to the appearance data $P_3(t)$ and the appearance data $P_6(t)$. FIG. 25 is a graph obtained by overlapping the appearance data $P_3(t)$ and the appearance data $P_6(t)$. According to the appearance data $P_6(t)$, the aggregated data belonging to the cluster $G_6$ appears at night. Further, according to the appearance data $P_3(t)$, the aggregated data belonging to the cluster G3 appears at midnight or early in the morning. Then, compared with the behavior of the user on the first day, the appearance time zone of the aggregated data related to the cluster $G_6$ coincides with the time zone of sleeping, and the appearance time zone of the aggregated data related to the cluster $G_3$ coincides with the time zone before and after going to bed and before and after getting up. From this, it is considered that the appearance data $P_6(t)$ represents a deep sleep state, and the appearance data $P_3(t)$ represents a shallow sleep state, respectively. As seen in FIG. 15, the clusters $G_3$ and $G_6$ all have low metabolic intensity and are appropriate as a sleep state.

Figure 26:
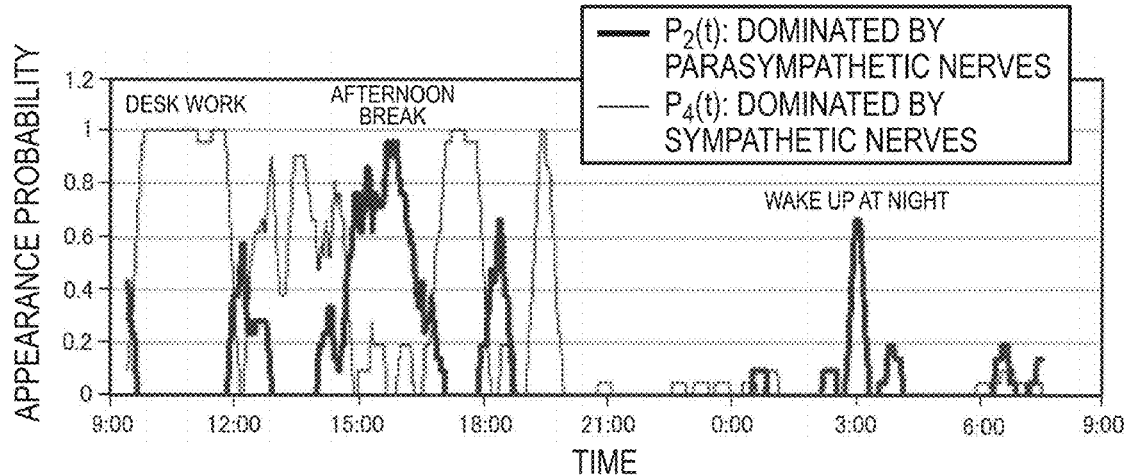
FIG. 26 is a graph obtained by overlapping the appearance data $P_2(t)$ and the appearance data $P_4(t)$.

Next, attention is paid to the appearance data $P_2(t)$ and the appearance data $P_4(t)$. FIG. 26 is a graph obtained by overlapping the appearance data $P_2(t)$ and the appearance data $P_4(t)$. According to these appearance data $P_2(t)$ and $P_4(t)$, aggregated data belonging to the clusters $G_2$ and $G_4$ all appear in the activity time zone during the daytime. Then, compared with the behavior of the user on the first day, the appearance time zone of the aggregated data related to the cluster $G_4$ coincides with the time zone such as the desk work, and the appearance time zone of the aggregated data related to the cluster $G_2$ coincides with a break time zone. From this, it is considered that the appearance data $P_2(t)$ represents a relaxed state dominated by parasympathetic nerves, and the appearance data $P_4(t)$ represents a concentrated state (awaken time) dominated by sympathetic nerves. As seen in FIG. 15, the cluster $G_4$ is dominated by sympathetic nerves and the cluster $G_2$ is dominated by parasympathetic nerves.

As described above, according to the appearance data generation process, the appearance data $P_c(t)$ of each cluster G1 to G6 can be associated with the state of the living body, by combining the first principal component $Y1(t)$ representing the metabolic intensity and the second principal component $Y_2(t)$ representing the degree of autonomic nervous function. Therefore, it is possible to correctly recognize the state of the living body at the corresponding time t, from the values of the plurality of pieces of biometric information measured at each time t.

The relationship between the appearance data $P_c(t)$ of each of the clusters $G_1$ to $G_6$ generated as described above and the state of the living body can also be obtained by performing a known regression analysis or the like. For example, a relative value C(t) representing the state of the living body of each appearance data $P_c(t)$ is obtained by using another measurement method. Then, a regression analysis is performed using the obtained relative value C(t) as a target variable and the appearance data $P_c(t)$ as an explanatory variable. More specifically, there is a method for obtaining a coefficient vector value β by applying a regression analysis by applying the following equation (2) to the relative value C(t) representing the state of each living body, by a least squares method or the like.

$$C(t)=\beta_1 P_1(t)+\beta_2 P_2(t)+ \ldots +\beta_s P_s(t) \tag{2}$$

It is also assumed a case where it is difficult to digitize the relative value C(t) representing the state of the living body. In that case, for example, in a case where the state of the living body is an operation such as "walking", "sitting", and "standing" of the user, by photographing the user with a video camera and analyzing the video, the presence or absence (presence=1 and absence=0) of these operations is specified at the time t. Then, the specified values may be averaged over time in the same manner as when generating the appearance data $P_c(t)$ from the cluster membership degree data $B_c(t)$ to obtain the relative value C(t).

(4) Display Control Process

Figure 27:
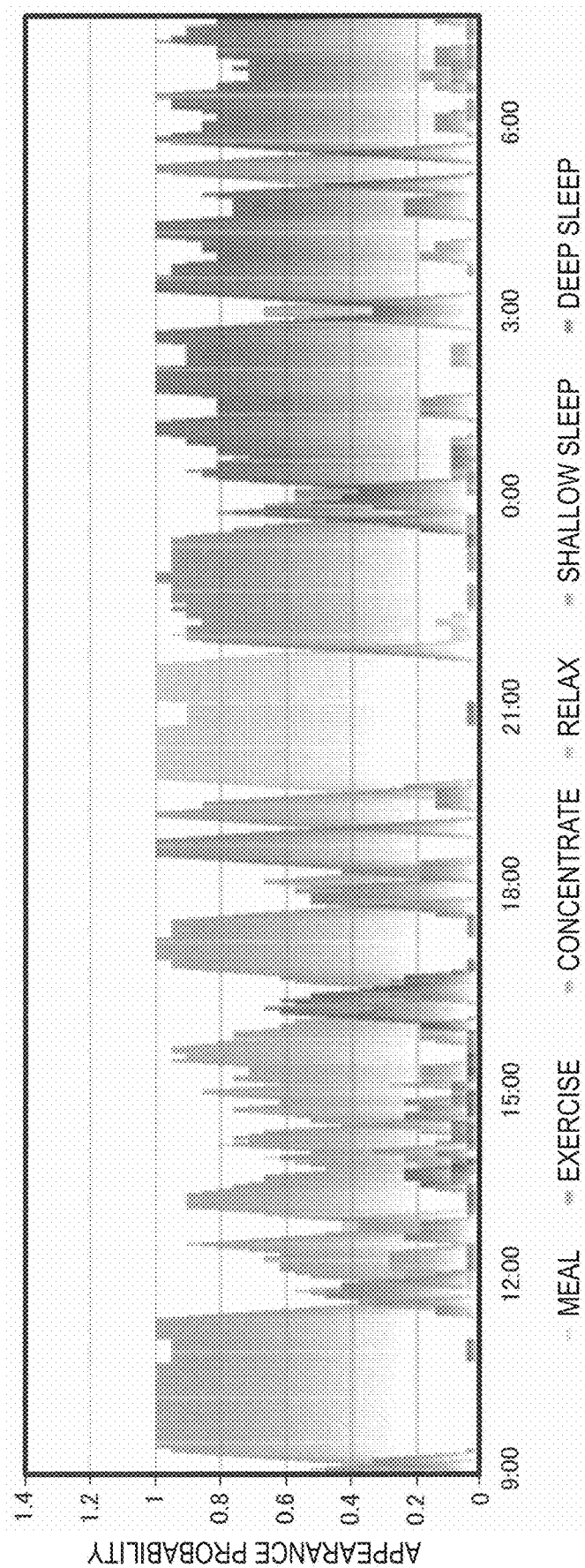
FIG. 27 is a diagram showing a display example of a state analysis result in the data processing apparatus.

After analyzing the state of the living body as described above, the data processing apparatus 5 performs control to display the state analysis result. FIG. 27 is a diagram showing a display example of the state analysis result. As shown in FIG. 27, for example, the state analysis result is displayed by displaying the graphs of each appearance data $P_c(t)$ shown in FIGS. 18 to 23 on a common time axis. Specifically, for each appearance data $P_c(t)$, the area inside the graph is filled with different display colors, and each area is displayed so as to be identifiable. At that time, in order to improve the visibility of the other appearance data $P_c(t)$ to be overlapped, the transmittance of filling may be adjusted. Since it is of course preferable that each appearance data $P_c(t)$ can be identified, each appearance data $P_c(t)$ may be identified and displayed by changing the line type or the display color of the graph, in addition to the filling of the area inside the graph. Further, the display color may be fixed, or may be set variably according to the operation input by the user.

Figure 28:
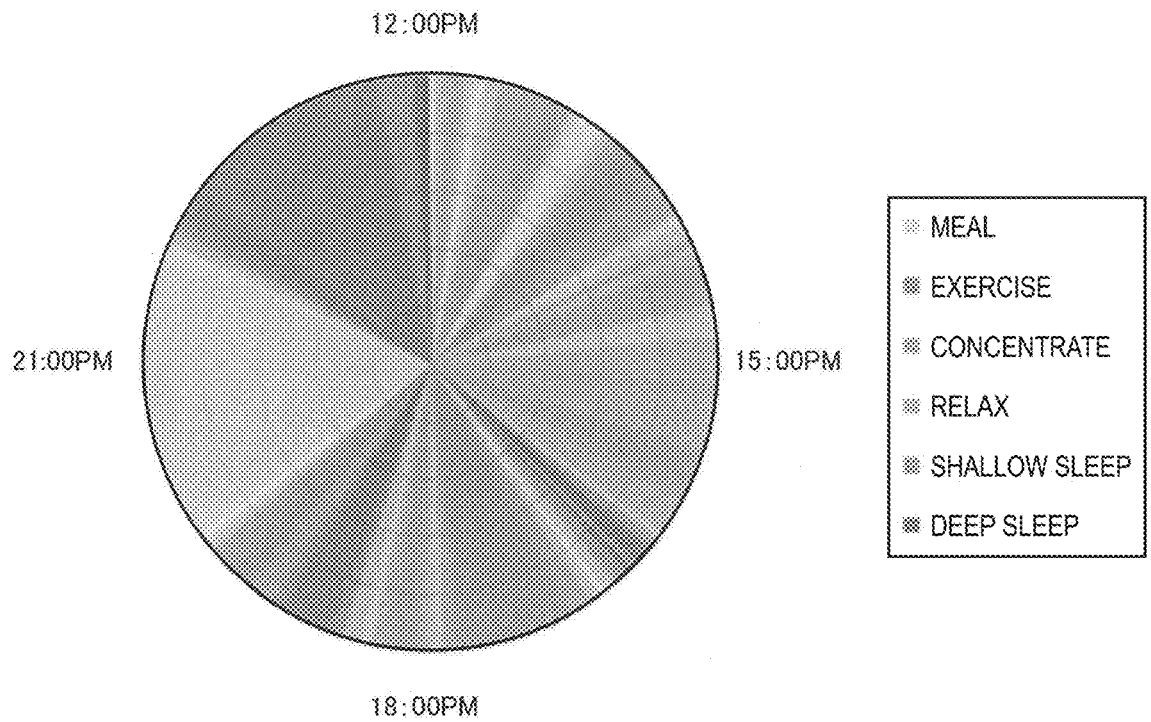
FIG. 28 is a diagram showing another display example of the state analysis result in the data processing apparatus.
Figure 29:
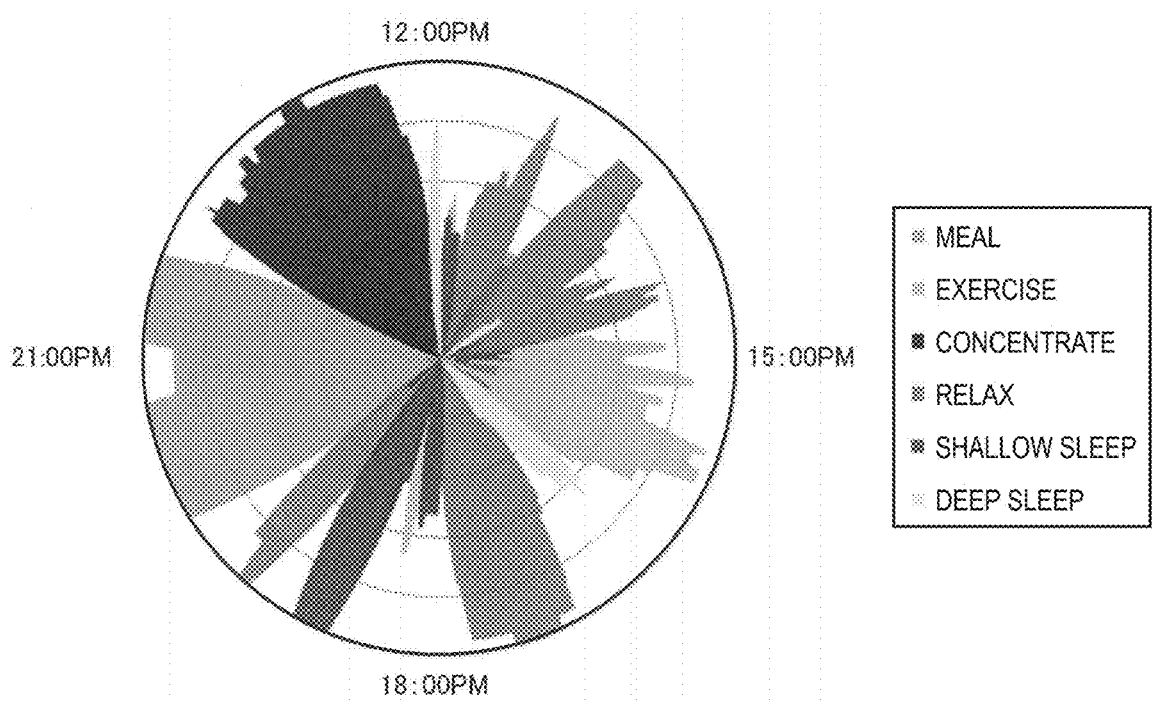
FIG. 29 is a diagram showing still another display example of the state analysis result in the data processing apparatus.

Note that the display form of FIG. 27 is merely an example, and the display form of the state analysis result is not particularly limited. For example, it may be displayed in the form of a dial with a time axis in the circumferential direction. The display example is shown in FIGS. 28 and 29. For example, as shown in FIG. 28, each appearance data $P_c(t)$ for half a day with 360 degrees as 12 hours may be displayed in a pie chart by associating the angle with the time t in the circumferential direction. Even in this case, a different display color is applied to each appearance data $P_c(t)$. In addition, the shade of the display color is adjusted according to the appearance probability at the corresponding time t. For example, as the value of appearance probability increases, it is adjusted to become darker (as the value of appearance probability decreases, it is adjusted to become thinner). The time range to be displayed is, for example, 12 hours back from the current time. Alternatively, 12 hours of the morning and 12 hours of the afternoon on the designated date may be switched and displayed, or may be displayed side by side, by receiving the operation input by the user.

For example, as shown in FIG. 29, each appearance data $P_c(t)$ may be displayed in a radar chart by associating the angle with the time t in the circumferential direction. The color coding and the shading of display colors and the display time ranges are the same as in the case of the pie chart display. According to the pie chart display or the radar chart display of each appearance data $P_c(t)$, the user can more intuitively recognize the state change with the lapse of time, or the degree of the state indicated by the appearance probability of the living body.

In addition, the graphs of each appearance data $P_c(t)$ shown in FIGS. 18 to 23 may be switched and displayed in accordance with the operation input by the user, or the respective graphs may be displayed side by side. Further, the user may select the display form of the state analysis result from among the various display forms. In addition, the display of the state analysis result is not limited to the case of the display of the appearance data $P_c(t)$. For example, a regression analysis is performed for each of the clusters G1 to G6, and time series regression analysis data C(t) obtained by Expression (2) may be displayed in the above-described various display forms.

Figure 30:
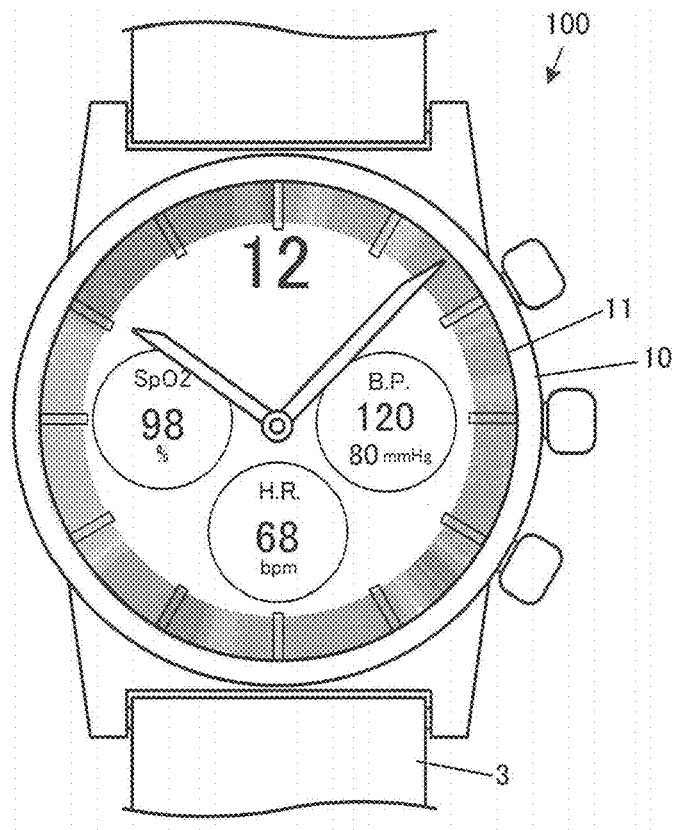
FIG. 30 is a diagram showing a display example of a state analysis result in the measuring apparatus.
Figure 31:
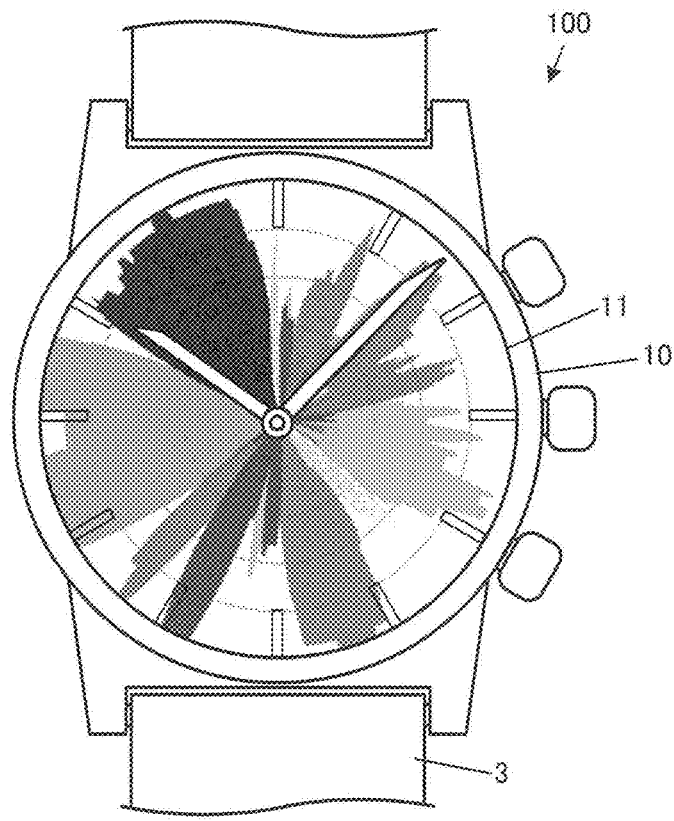
FIG. 31 is a diagram showing another display example of the state analysis result in the measuring apparatus.
Figure 32:
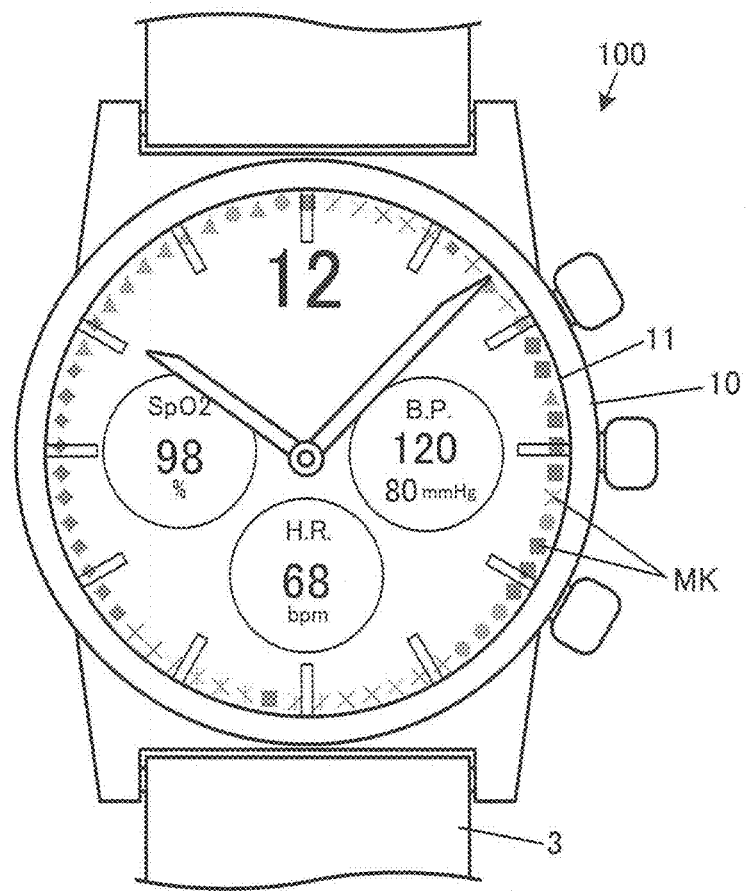
FIG. 32 is a diagram showing still another display example of the state analysis result in the measuring apparatus.

Further, the data processing apparatus 5 may transmit the analysis result to the measuring apparatus 100, and the state analysis result may be displayed by the measuring apparatus 100. Alternatively, the analysis result may be transferred to electronic devices other than the data processing apparatus 5 and the measuring apparatus 100, and displayed on the display device thereof. For example, in the case of displaying the analysis result on the measuring apparatus 100, by displaying the appearance data $P_c(t)$ of each of the clusters $G_1$ to $G_6$ on the liquid crystal panel disposed on the front surface of the dial 11 in the form of a dial, the state analysis result can be displayed together with the current time. FIGS. 30 to 32 are diagrams showing a display example of a state analysis result in the measuring apparatus 100.

For example, as shown in FIG. 30, the outer peripheral portion of the pie chart in FIG. 28 may be displayed on the dial 11. Alternatively, as shown in FIG. 31, a radar chart similar to FIG. 29 may be displayed on the dial 11. Although not shown, a pie chart similar to that in FIG. 28 may be displayed on the dial 11.

Alternatively, as shown in FIG. 32, a representative value mark MK representing the representative value of each appearance data $P_c(t)$ may be displayed at the position of the scale of time along the outer periphery of the dial 11. In this case, the appearance data $P_c(t)$ is sequentially processed, and the display time range is divided by unit time such as 1 [min] to calculate the average value of appearance probabilities at each time t. Without being limited to the average value, the mode value within the unit time may be calculated. Subsequently, the maximum value out of the average values of each appearance data $P_c(t)$ is selected for each unit time and is set as the representative value in the corresponding unit time. Then, control is performed to display the representative value mark MK based on the representative value. Specifically, the display color is set to a display color corresponding to the cluster of the source of the representative value, and the shading is adjusted based on the representative value.

Functional Configuration

Figure 33:
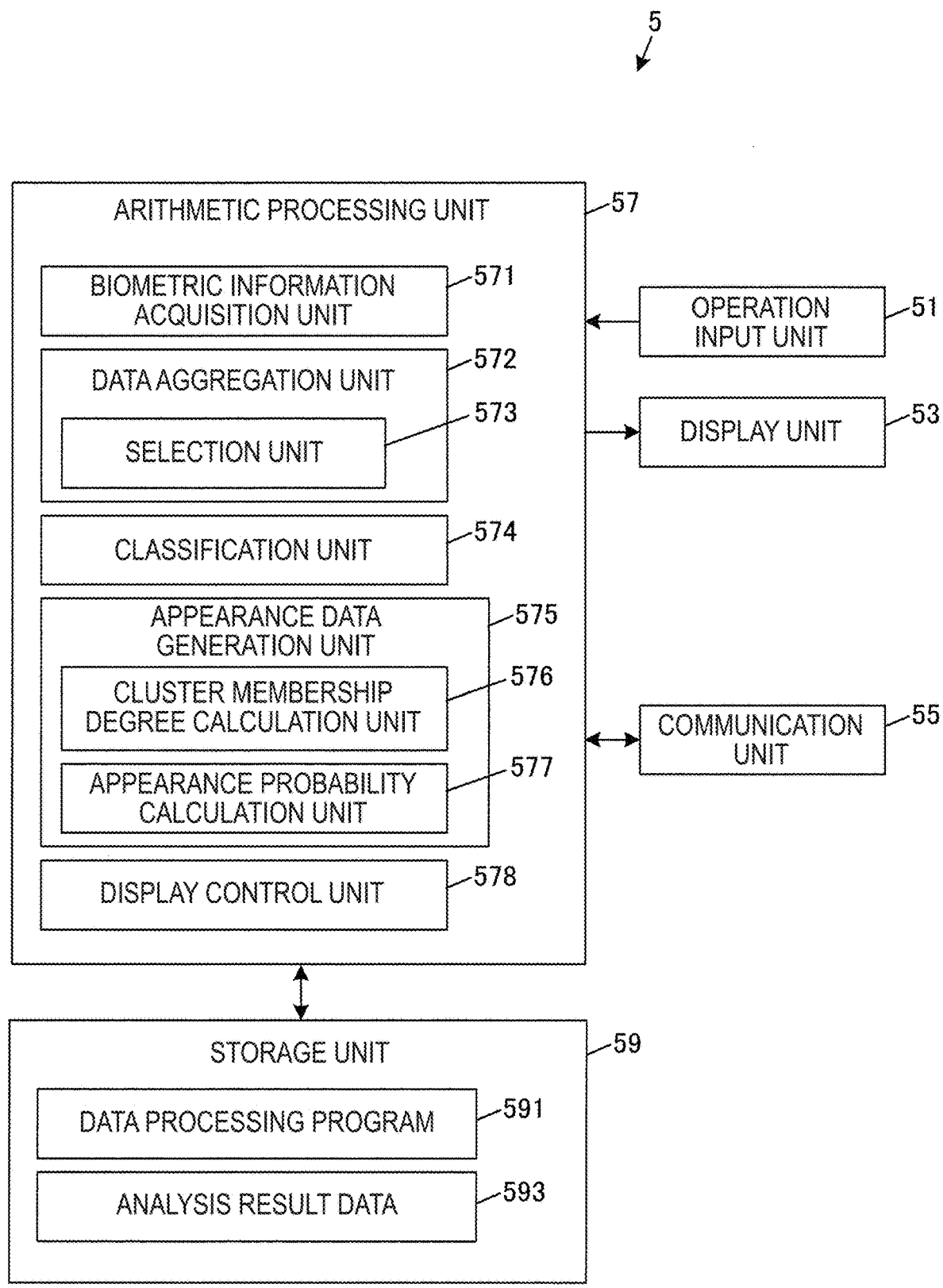
FIG. 33 is a block diagram showing a main functional configuration example of the data processing apparatus.

FIG. 33 is a block diagram showing a main functional configuration example of the data processing apparatus. As shown in FIG. 33, the data processing apparatus 5 includes an operation input unit 51, a display unit 53, a communication unit 55, a arithmetic processing unit 57, and a storage unit 59.

The operation input unit 51 receives various operation inputs by the user, and outputs an operation input signal corresponding to the operation input to the arithmetic processing unit 57. The operation input unit 51 can be realized by a button switch, a lever switch, a dial switch, a touch panel, or the like.

The display unit 53 is realized by a display device such as a liquid crystal display (LCD), an organic electroluminescence display (OELD), and an electronic paper display, and performs various displays based on a display signal from the arithmetic processing unit 57.

The communication unit 55 is a communication device for exchanging data with the outside (for example, the measuring apparatus 100) under the control of the arithmetic processing unit 57. As the communication system of the communication unit 55, a type of a wireless connection using wireless communication, a type of wired connection through a cable conforming to a predetermined communication standard, a type of connection through an intermediate device also serving as a charger called a cradle, and the like can be applied.

The arithmetic processing unit 57 performs input and output control of data between functional units, and executes various arithmetic processes, based on predetermined programs and data, operation input signals from the operation input unit 51, the biometric information $S_n(t)$ acquired from the measuring apparatus 100 through the communication unit 55, and the like. For example, the arithmetic processing unit 57 is realized by a microprocessor such as a central processing unit (CPU) or a graphics processing unit (GPU), or an electronic component such as an application specific integrated circuit (ASIC), a field programmable gate array (FPGA), and an integrated circuit (IC) memory.

The arithmetic processing unit 57 includes a biometric information acquisition unit 571, a data aggregation unit 572, a classification unit 574, an appearance data generation unit 575, and a display control unit 578.

The biometric information acquisition unit 571 controls data communication with the measuring apparatus 100, and acquires the biometric information $S_n(t)$ from the measuring apparatus 100 through the communication unit 55.

The data aggregation unit 572 executes a principal component analysis on the N types of (in the first embodiment, four types of the heat flux, the wrist temperature, the oxygen saturation level in arterial blood, and the pulse rate) of biometric information $S_n(t)$ to obtain the first principal component $Y_1(t)$ to the X-th principal component $Y_X(t)$, which are aggregated into X types of classification time series data. The data aggregation unit 572 includes a selection unit 573 that selects M types from X types of classification time series data. In the first embodiment, the first principal component $Y_1(t)$ and the second principal component $Y_2(t)$ are selected.

The classification unit 574 plots the aggregated data of the first principal component $Y_1(t)$ and the second principal component $Y_2(t)$ in the two-dimensional space, and classifies each aggregated data into a plurality (for example, six) clusters $G_1$ to $G_6$, based on the distances in the two-dimensional space.

The appearance data generation unit 575 generates the appearance data $P_c(t)$ of each of the clusters $G_1$ to $G_6$. The appearance data generation unit 575 includes a cluster membership degree calculation unit 576 and an appearance probability calculation unit 577. The cluster membership degree calculation unit 576 generates the cluster membership degree data $B_c(t)$ in time series determined for each of the clusters $G_1$ to $G_6$ as to whether or not the cluster to which each aggregated data belongs is the own cluster. The appearance probability calculation unit 577 sequentially processes and averages the cluster membership degree data $B_c(t)$ at a predetermined time width while shifting the calculation time to calculate the appearance probability for each calculation time.

The display control unit 578 performs control of displaying appearance data $P_c(t)$ of each of the clusters $G_1$ to $G_6$ generated by the appearance data generation unit 575 on the display unit 53 as a state analysis result of a living body.

The storage unit 59 is realized by a storage medium such as an IC memory, a hard disk, and an optical disk. In the storage unit 59, a program for operating the data processing apparatus 5 to realize various functions of the data processing apparatus 5, data to be used during execution of the program, or the like is stored in advance, or is temporarily stored every time processing is performed. Note that the connection between the arithmetic processing unit 57 and the storage unit 59 is not limited to the connection by the internal bus circuit in the apparatus, and may be realized by a communication line such as a local area network (LAN) or the Internet. In this case, the storage unit 59 may be realized by an external storage device different from the data processing apparatus 5.

Further, a data processing program 591 and analysis result data 593 are stored in the storage unit 59.

The arithmetic processing unit 57 realizes the functions of the biometric information acquisition unit 571, the data aggregation unit 572, the classification unit 574, the appearance data generation unit 575, the display control unit 578, and the like, by reading and executing the data processing program 591. In addition, although it is described that each of these units is realized by software by the arithmetic processing unit 57 reading and executing the data processing program 591, each unit can be realized by hardware by configuring an electronic circuit dedicated to each unit.

In the analysis result data 593, the appearance data $P_c(t)$ of each of the clusters $G_1$ to $G_6$ and regression analysis data $C(t)$ are stored as a state analysis result of a living body.

Process Flow

Figure 34:
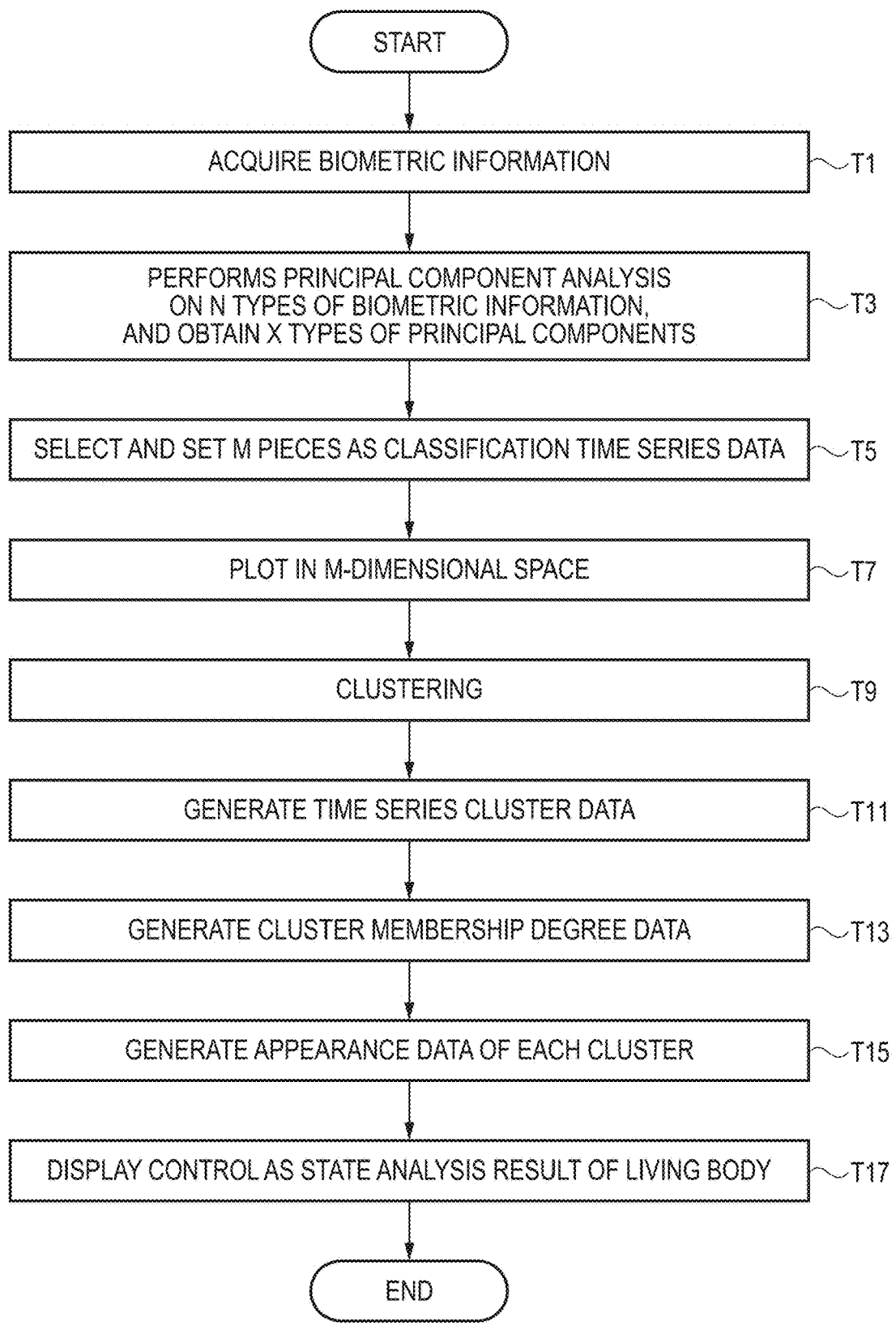
FIG. 34 is a flowchart showing a flow of a process performed by the data processing apparatus.

FIG. 34 is a flowchart showing a flow of a process performed by the data processing apparatus 5. The process described here can be realized by the arithmetic processing unit 57 reading out and executing the data processing program 591 from the storage unit 59 and operating each unit of the data processing apparatus 5.

First, the biometric information acquisition unit 571 controls data communication with the measuring apparatus 100, and acquires the biometric information $S_n(t)$ measured in time series by the measuring apparatus 100 (step T1).

Next, the data aggregation unit 572 performs principal component analysis on the four types of biometric information $S_n(t)$, for example, the heat flux, the wrist temperature, the oxygen saturation level in arterial blood, and the pulse rate, from among the biometric information acquired in step T1, and obtains the principal components $Y_1(t)$ to X-th principal component $Y_X(t)$ (step T3). Then, the selection unit 573 selects M pieces, for example, the first principal component $Y_1(t)$ and the second principal component $Y_2(t)$, from the obtained X types of principal components $Y_1(t)$ to $Y_X(t)$, and sets M types of classification time series data (step T5).

Next, the classification unit 574 plots the first principal component $Y_1(t)$ and the second principal component $Y_2(t)$ selected in step T5 as a pair (aggregated data) for each time t in a two-dimensional space (step T7). Then, each plotted aggregated data is clustered and classified into a plurality of clusters $G_1$ to $G_6$ (step T9).

Next, in the appearance data generation unit 575, the cluster membership degree calculation unit 576 generates time series cluster data c(t) based on the classification result of the cluster (step T11). Then, time series cluster membership degree data Bc(t) is generated for each of the clusters $G_1$ to $G_6$ based on the time series cluster data c(t) (step T13). Thereafter, the appearance probability calculation unit 577 calculates the appearance probability for each calculation time based on each cluster membership degree data $B_c(t)$ with respect to each of the clusters $G_1$ to $G_6$ to generate the appearance data $P_c(t)$ for each of the clusters $G_1$ to $G_6$ (Step T15).

After generating the appearance data $P_c(t)$, the display control unit 578 performs control to display it on the display unit 53 as a state analysis result of the living body (step T17).

As described above, according to the first embodiment, it is possible to analyze the state of the living body represented by the appearance data $P_c(t)$ of each of the clusters $G_1$ to $G_6$, in consideration of N types of biometric information $S_n(t)$ different in unit and concept from each other in a complex manner.

Second Embodiment

In the second embodiment, purchaser information of a product in a retail store is processed as sampling time series data of N types (N≥3), for example, a customer who visited the retail store is analyzed. The purchaser information includes customer information such as age, sex, and address, which are obtained in advance from the purchaser (customer). The customer information can be collected at the time of creation of a point card in a case of a real store, at the time of member registration prior to purchase in a case of an online store. By associating the point card or the membership registration information with the purchased product at the time of purchasing the product, it is possible to collect information on when and which product each purchaser purchased. Hereinafter, a simulation example of customer analysis based on purchaser information in a real store will be described.

Principle

Figure 35:
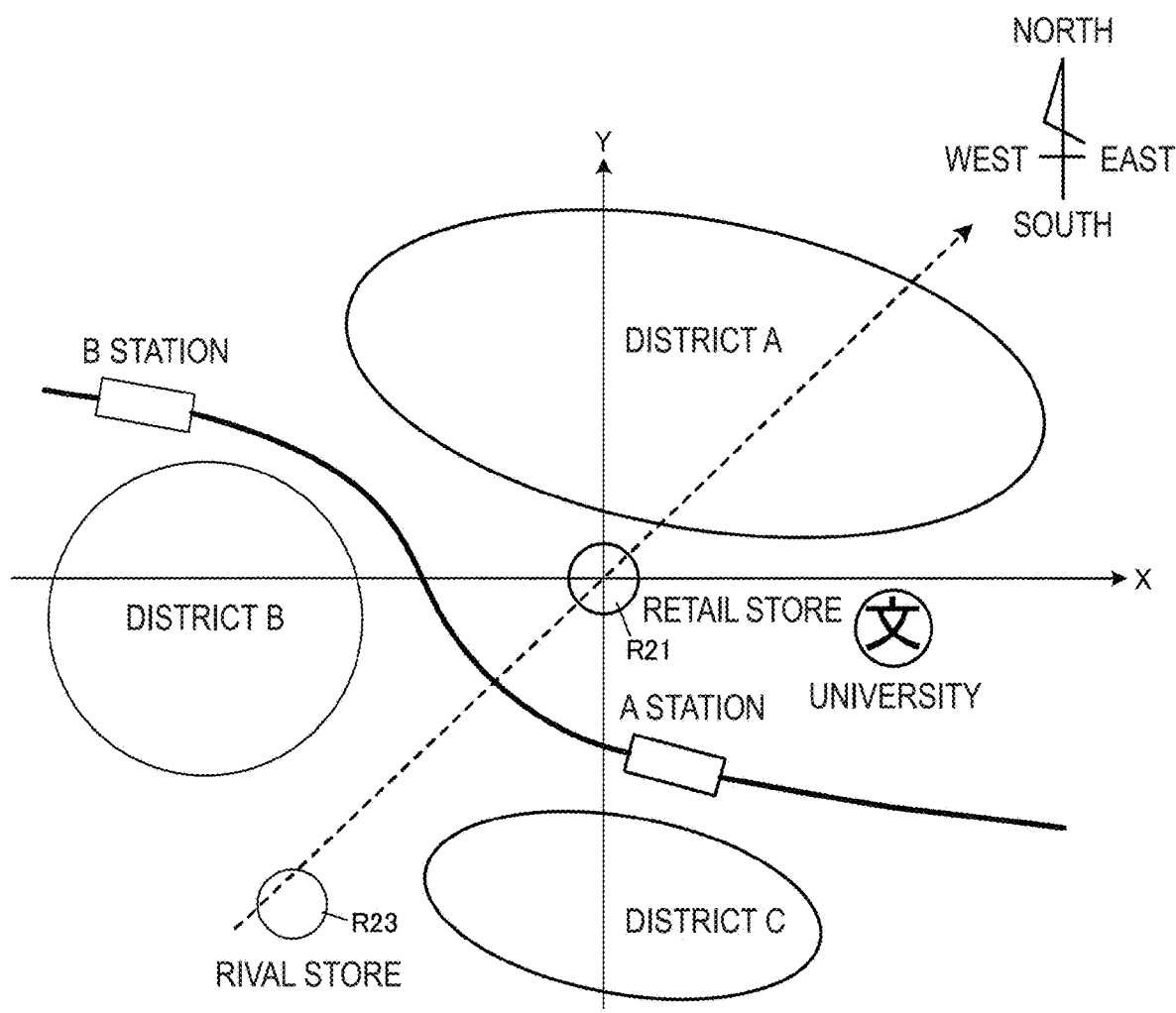
FIG. 35 is a diagram showing a peripheral map of an XY coordinate system with a retail store as an origin.

FIG. 35 is a diagram showing a peripheral map of a planar XY coordinate system with a retail store R21 as an origin. In this example, the retail store R21 is located near the A station along the railroad. In the surrounding area, there is a district with detached houses (detached residential district) A, a district with many single apartments (the single apartment district) B, and a district which is a high-class residential area, and where a lot of elderly people live (high-class residential area district) C. In addition, a university is located in the east direction, and a competing rival store R23 is located in the southwest direction across the railroad track.

Figure 37:
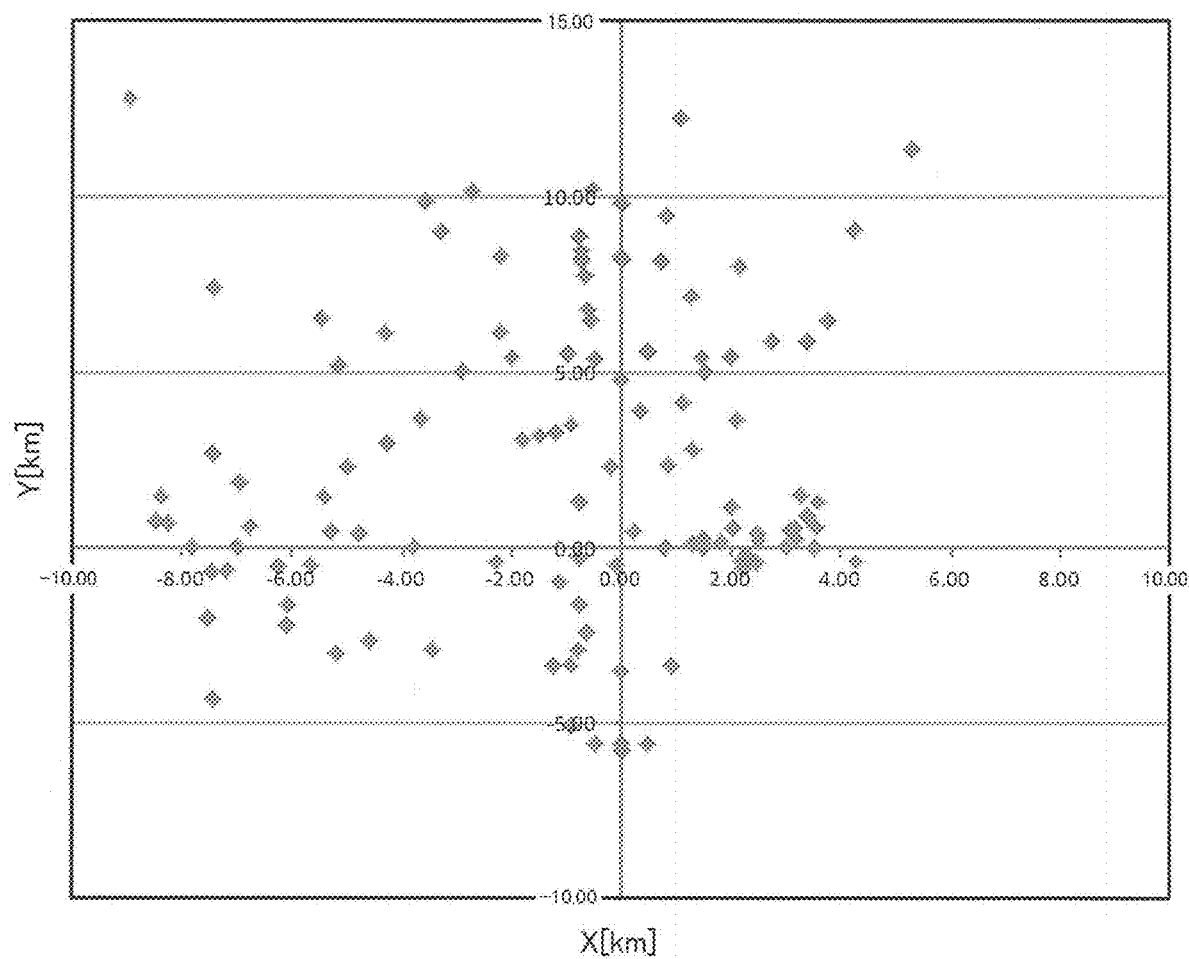
FIG. 37 is a diagram showing a distribution example of the residence coordinates (X, Y) of a customer.

FIG. 36 is a diagram showing an example of purchaser information $S_n(t)$ for one day as sampling data, in which each piece of purchaser information $S_n(t)$ is tabulated and shown in association with time t which is a purchase time. Further, FIG. 37 is a diagram showing a distribution example of the residence coordinates (X, Y) of a customer, which is the purchaser information $S_n(t)$. In the second embodiment, four types of purchaser information $S_n(t)$ of the age of the purchaser as $S_1(t)$, the X coordinate of the residential place specified from the address of the purchaser as $S_2(t)$, the Y coordinate of the residential place as $S_3(t)$, and the purchase price as $S_4(t)$ are used for customer analysis. Each piece of purchaser information $S_n(t)$ can be acquired by generating data for one record each time a product is purchased at the retail store R21. In the customer analysis, as shown in FIG. 36, for example, records are extracted every 5 [min] and used.

The procedure itself of the client analysis is the same as the procedure of the state analysis of a living body in the first embodiment, and a data processing apparatus 5b (see FIG. 42) of the second embodiment, first, executes the principal component analysis on the purchaser information $S_n(t)$ and aggregates them to acquire classification time series data of M types (M≥2 and N>M). Then, customer analysis is executed (2) by classifying the acquired classification time series data into clusters, and (3) generating appearance data in time series for each classified cluster. The customer analysis result is (4) displayed, for example, on the data processing apparatus 5b, and presented to the user.

(1) Data Aggregation Process

In the data aggregation process, four types of purchaser information $S_n(t)$ of an age $S_1(t)$, an X coordinate $S_2(t)$, a Y coordinate $S_3(t)$, and a purchase price $S_4(t)$ are normalized and used, and the principal component analysis of the purchaser information $S_n(t)$ is executed. FIG. 38 shows the coefficient vector value $\alpha_{1n}$ related to each piece of purchaser information $S_n(t)$ defining the first principal component $Y_1(t)$ and the coefficient vector value $\alpha_{2n}$ related to each piece of purchaser information $S_n(t)$ defining the second principal component $Y_2(t)$.

As described in the first embodiment, the coefficient vector value $\alpha_{1n}$ represents the degree of influence on the first principal component $Y_1(t)$ of the corresponding purchaser information $S_n(t)$, and the coefficient vector value $\alpha_{2n}$ represents the degree of influence on the second principal component $Y_2(t)$ of the corresponding purchaser information $S_n(t)$. Then, the meaning of each principal component is inferred from the values of the coefficient vector values $\alpha_{1n}$ and $\alpha_{2n}$. First, in the first principal component $Y_1(t)$, the coefficient vector value $\alpha_{11}$ related to the age and the coefficient vector value $\alpha_{14}$ related to the purchase price are large and are positive values of the same degree. This is considered because there is a correlation between the age and the purchase price, and the first principal component $Y_1(t)$ can be interpreted as a measure showing correlation (hereinafter referred to as "economic age indicator").

Next, regarding the second principal component $Y_2(t)$, both the coefficient vector value $\alpha_{22}$ related to the X coordinate and the coefficient vector value $\alpha_{23}$ related to the Y coordinate have large positive values and positive values. According to this, the second principal component $Y_2(t)$ can be interpreted as a measure correlating with the direction of X:Y=1:1, that is, the northeast direction of the dashed arrow shown in FIG. 35 (hereinafter, referred to as "northeast direction distance indicator").

As described above, according to the data aggregation process, the N types of purchaser information are subjected to, for example, a principal component analysis to extract principal components and can be aggregated into M types of classification time series data (here, an economic age indicator and a northeast direction distance indicator) useful for customer analysis.

(2) Classification Process

Figure 39:
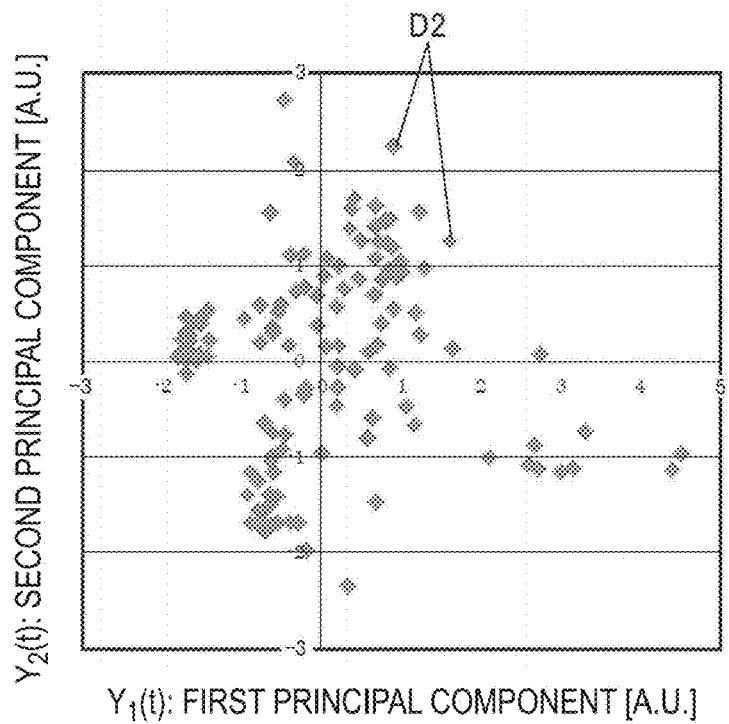
FIG. 39 is a diagram plotting aggregated data of the first principal component $Y_1(t)$ and the second principal component $Y_2(t)$ in the second embodiment.

In a classification processing, first, M types of classification time series data acquired by data aggregation process are plotted in an M-dimensional space. For example, the first principal component $Y_1(t)$ and the second principal component $Y_2(t)$ are made into a pair at each time t ($t_1$, $t_2$, and the pairs are plotted in a two-dimensional space as aggregate data of the purchaser information $S_n(t)$ in the record at the corresponding time t (FIG. 36). FIG. 39 is a diagram in which each aggregated data D2 is plotted with the horizontal axis as the first principal component $Y_1(t)$ and the vertical axis as the second principal component $Y_2(t)$.

Figure 40:
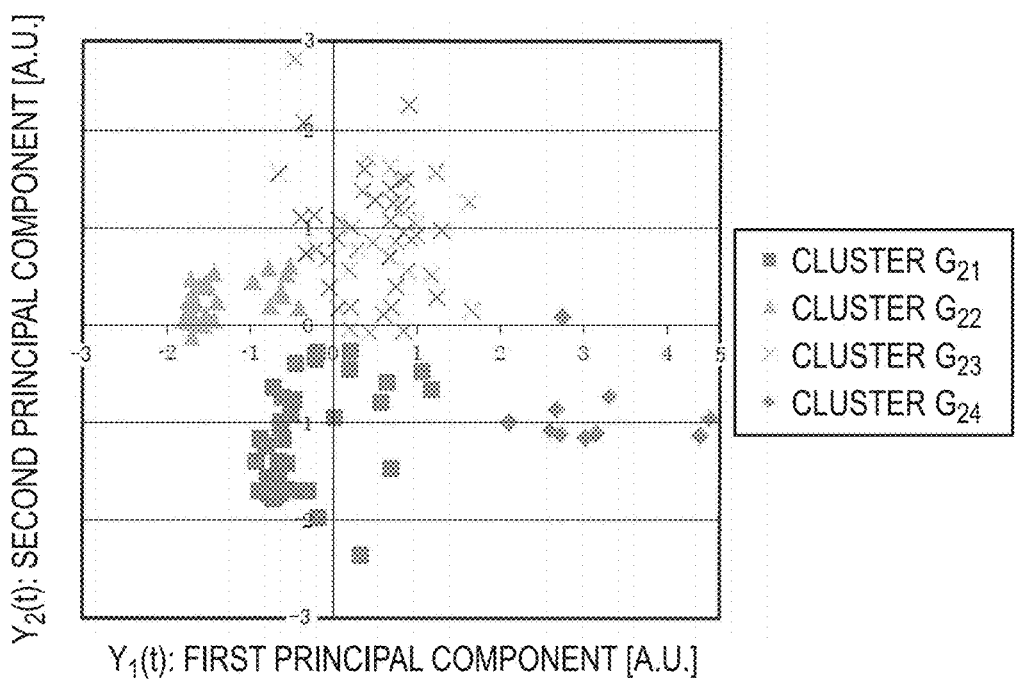
FIG. 40 is a diagram showing a clustering result of the aggregated data of FIG. 39.

Once aggregated data is plotted, clustering is performed to classify each aggregated data into s clusters. FIG. 40 is a diagram showing the clustering result, which shows four clusters $G_{21}$ to $G_{24}$ obtained by classifying each aggregated data D2 in FIG. 39 with s=4. Here, since the first principal component $Y_1(t)$ on the horizontal axis is the economic age indicator and the second principal component $Y_2(t)$ on the vertical axis is the northeast direction distance indicator, it is considered that each of the clusters $G_{21}$ to $G_{24}$ corresponds to the customer's residential area classification.

That is, the cluster $G_{21}$ has a somewhat lower economic age indicator. Also, since the northeast direction distance indicator is a negative value, it correlates with the opposite southwest direction. As can be seen from FIG. 35, since there is the single apartment district B in the southwest direction of the retail store R21, it is considered that the single apartment district B corresponds to the cluster $G_{21}$.

Next, the cluster $G_{22}$ has a low economic age indicator. In addition, it is considered that the northeast direction distance indicator is around "0" and corresponds to a customer living near the retail store R21. Since there is a university near the retail store R21, it is considered that university officials correspond to the cluster $G_{22}$.

Next, the cluster $G_{23}$ has a medium economic age indicator, and its aggregate data is widely distributed in the northeast direction. Since there is a detached residential district A in the northeast direction of the retail store R21, the detached residential district A has a large area, so it is considered that the detached residential district A corresponds to the cluster $G_{23}$.

Next, the cluster $G_{24}$ has a high economic age indicator. Further, since the northeast direction distance indicator is a negative value, it correlates with the southwest direction. Further, since in the southwest direction, there is a high-class residential area district C in the southwest direction somewhat away from the retail store R21, it is considered that the high-class residential area district C corresponds to the cluster $G_{24}$.

As described above, in the second embodiment, it is possible to specify the customer's residential area classification corresponding to the clusters $G_{21}$ to $G_{24}$ from the combination of the first principal component $Y_1(t)$ representing the economic age indicator and the second principal component $Y_2(t)$ representing the northeast direction distance indicator as a result of the classification process.

(3) Appearance Data Generation Process

In the appearance data generation process, first, time series cluster data c(t) is generated based on the classification result of the cluster. Subsequently, based on the time series cluster data c(t), the cluster membership degree data $B_c(t)$ (c=1, 2, ..., s) in time series determined for each of the clusters $G_{21}$ to $G_{24}$ as to whether or not the cluster to which each aggregated data D2 belongs is the own cluster. Then, based on each cluster membership degree data $B_c(t)$, the appearance data $P_c(t)$ of each of the clusters $G_{21}$ to $G_{24}$ is generated.

Figure 41:
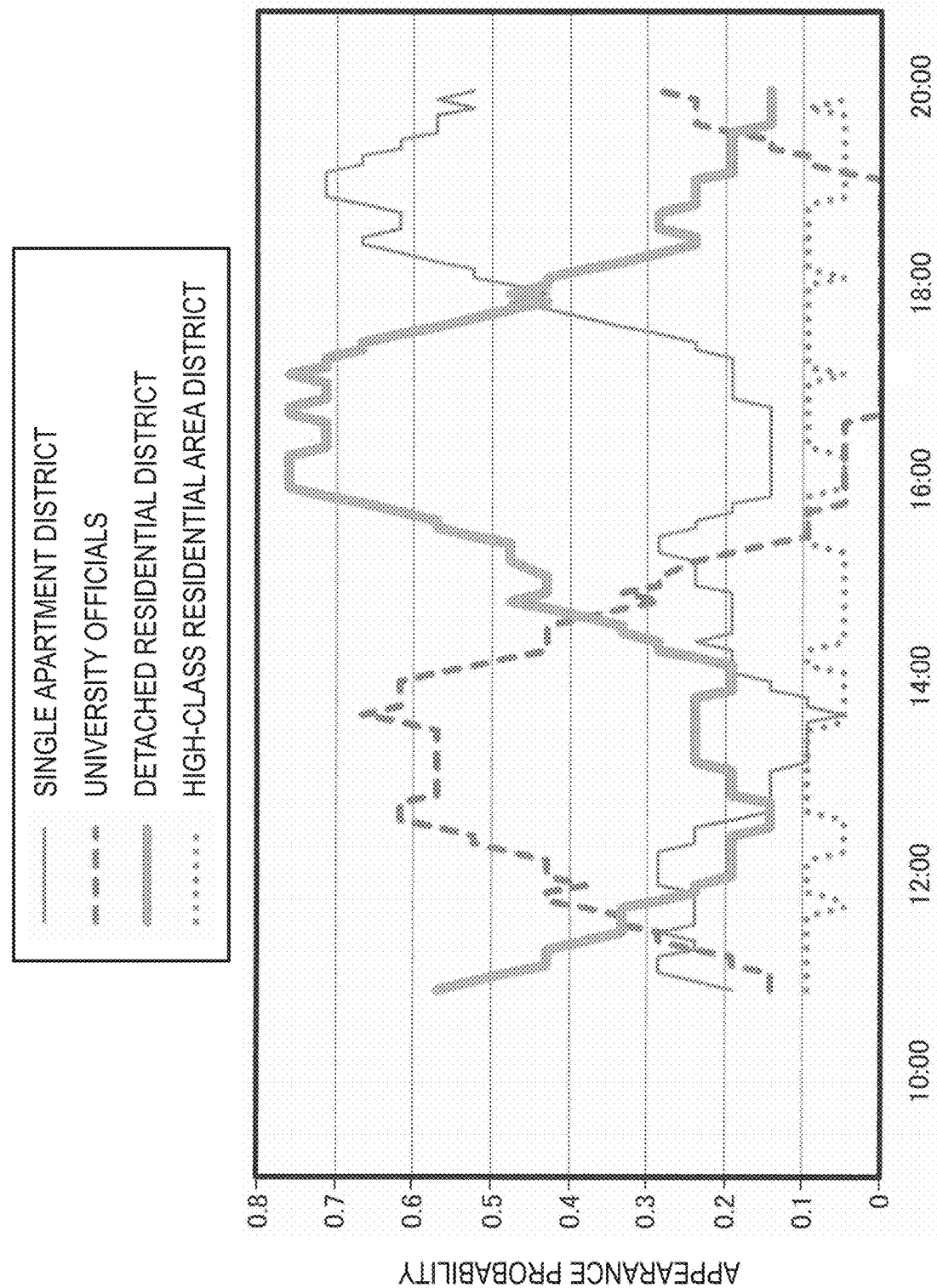
FIG. 41 is a graph obtained by overlapping appearance data $P_c(t)$ of clusters $G_{21}$ to $G_{24}$ on a common time axis.

FIG. 41 is a graph obtained by overlapping appearance data $P_c(t)$ of clusters $G_{21}$ to $G_{24}$ on a common time axis. According to FIG. 41, for the cluster $G_{21}$, $G_{22}$, and $G_{23}$ among the cluster $G_{21}$ to $G_{24}$, it is found that the aggregated data appeared unevenly temporally.

Specifically, according to the appearance data $P_1(t)$, it is understood that many pieces of aggregated data belonging to the cluster $G_{21}$ appear in the evening and at night, and the customers from the single apartment district B among the customers of the retail store R21 use the retail store R21 in a time zone from the evening to the night. In addition, according to the appearance data $P_2(t)$, it is found that many pieces of aggregated data belonging to the cluster $G_{22}$ appear around noon and university officials use the retail store R21 during lunch break. Further, according to the appearance data P3 (t), many pieces of aggregated data belonging to the cluster G23 appear in the morning and evening, and it is considered that the customers of the detached residential district A use the retail store R21 for shopping of everyday items. According to the appearance data $P_4(t)$, since there is little feature in the temporal appearance trend of the aggregated data belonging to the cluster $G_{24}$ and the appearance probability is small overall, it is considered that the number of customers from the high-class residential area district C is small. This suggests that the southwest rival store may deprive of customers.

As described above, according to the appearance data generation process, the appearance data $P_c(t)$ of each of the clusters $G_{21}$ to $G_{24}$ can be associated with the state of the customer's visit to the retail store R21 in the residential area classification corresponding to each of the clusters $G_{21}$ to $G_{24}$. Therefore, it is possible to correctly recognize the state of customer's visit at the corresponding time t, from the values of the plurality of pieces of purchaser information $S_n(t)$ at each time t. In addition, customers are analyzed based on the recognized state of customer's visit and the type and the number of the products to be displayed are adjusted according to the customer layer in each time zone, which can contribute to sales improvement. For example, it can be used for retail store management, such as planning of giving a discount depending on day of the week, a time zone, or the like, for customers living in a specific district.

(4) Display Control Process

Also in the second embodiment, it is possible to realize the display control of the analysis result similar to that in the first embodiment. For example, the customer analysis result is displayed in such a manner that a graph of each appearance data $P_c(t)$ shown in FIG. 41 is displayed. Further, similar to the first embodiment, the customer analysis result may be transferred to electronic devices other than the data processing apparatus 5b, and displayed on the display device thereof.

Functional Configuration

Figure 42:
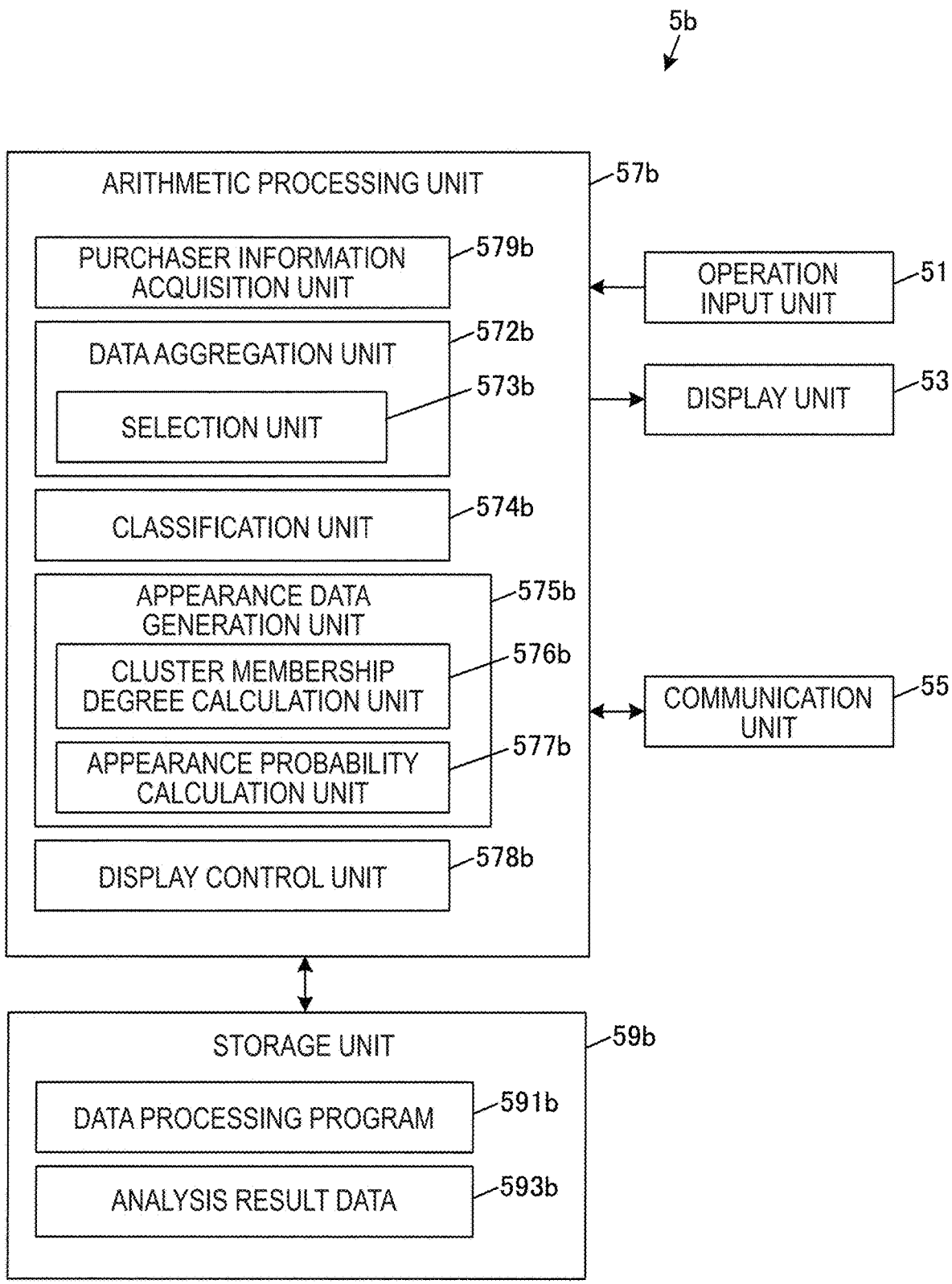
FIG. 42 is a block diagram illustrating a functional configuration example of a data processing apparatus according to the second embodiment.

FIG. 42 is a block diagram illustrating a functional configuration example of a data processing apparatus 5b according to the second embodiment. In FIG. 42, the same reference numerals are given to the same configuration components as in the first embodiment.

In the data processing apparatus 5b of the second embodiment, an arithmetic processing unit 57b includes a purchaser information acquisition unit 579b, a data aggregation unit 572b, a classification unit 574b, an appearance data generation unit 575b, and a display control unit 578b.

The purchaser information acquisition unit 579b controls data communication with an external device that manages, for example, customer information and sales history of the retail store R21, and acquires purchaser information $S_n(t)$ through the communication unit 55.

The data aggregation unit 572b executes the principal component analysis on the purchaser information $S_n(t)$ of N types (in the second embodiment, four types of an age, an X coordinate, a Y coordinate, and a purchase price) to obtain the first principal component $Y_1(t)$ to the X-th principal component $Y_X(t)$, which are aggregated into X types of classification time series data. Similar to the first embodiment, the data aggregation unit 572b includes a selection unit 573b that selects M types from X types of classification time series data. In the second embodiment, the first principal component $Y_1(t)$ and the second principal component $Y_2(t)$ are selected.

The classification unit 574b plots the aggregated data of the first principal component $Y_1(t)$ and the second principal component $Y_2(t)$ in the two-dimensional space, and classifies each aggregated data into a plurality (for example, four) clusters $G_{21}$ to $G_{24}$, based on the distances in the two-dimensional space.

The appearance data generation unit 575b generates the appearance data $P_c(t)$ of each of the clusters $G_{21}$ to $G_{24}$. Similar to the first embodiment, the appearance data generation unit 575b includes a cluster membership degree calculation unit 576b and an appearance probability calculation unit 577b.

The display control unit 578b performs control of displaying appearance data $P_c(t)$ of each of the clusters $G_{21}$ to $G_{24}$ generated by the appearance data generation unit 575b on the display unit 53 as a state analysis result of customers.

Further, a data processing program 591b and analysis result data 593b are stored in the storage unit 59b.

The arithmetic processing unit 57b realizes the functions of the purchaser information acquisition unit 579b, the data aggregation unit 572b, the classification unit 574b, the appearance data generation unit 575b, the display control unit 578b, and the like, by reading and executing the data processing program 591b. In the analysis result data 593b, the appearance data $P_c(t)$ of each of the clusters $G_{21}$ to $G_{24}$ and regression analysis data C(t) is stored as a customer analysis result.

Process Flow

Since the flow of the process performed by the data processing apparatus 5b is the same as the flow of the process performed by the data processing apparatus 5 of the first embodiment, the description thereof will be omitted.

As described above, according to the second embodiment, it is possible to analyze the state of customer's visit at each residential area district corresponding to each of the clusters $G_{21}$ to $G_{24}$, in consideration of N types of purchaser information $S_n(t)$ different in unit and concept from each other in a complex manner.

Modification Example

Although the embodiments to which the invention is applied have been described above, aspects to which the invention can be applied are not limited to the above-described embodiment. For example, the following modification examples are conceivable.

For example, the biometric information to be aggregated is not limited to the four types of a heat flux, a wrist temperature, an oxygen saturation level in arterial blood, and a pulse rate, which are illustrated in the first embodiment, and N types (N≥3) of biometric information may be selected appropriately and may be used as sampling data. In addition to the biometric information, environment information such as temperature, humidity, and atmospheric pressure may be included in the sampling data.

The principal components selected from the X types of principal components (classification time series data) $Y_1(t)$ to $Y_X(t)$ are not limited to two types of principal components including the first principal component and the second principal component, but three types or more (M≥2 and N>M) principal components may be selected. At this time, M types of principal components may be selected in descending order of the variance $l_1(t)$ to $l_X(t)$, from among the X types of main components $Y_1(t)$ to $Y_X(t)$.

Further, with respect to the number M of principal components to be selected, it is not limited to a configuration in which a preset predetermined number (two in the above embodiment) of principal components are selected. For example, M types of principal components may be selected by selecting principal components satisfying the selection condition, with the cumulative contribution ratio Rm expressed by the following Expression (3) being equal to or larger than a threshold value Tr as a selection condition. The threshold value Tr may be set in advance, for example, to be "0.8".

$$R_m \equiv \frac{l_1(t) + l_2(t) + \ldots l_m(t)}{l_1(t) + l_2(t) + \ldots l_y(t)} \geq Tr \quad (3)$$

Further, the method of aggregating the N types of sampling data (the biometric information in the first embodiment and the purchaser information in the second embodiment) into classification time series data is not limited to the principal component analysis. For example, a configuration may be adopted in which N types of sampling data are subjected to factor analysis and M types of common factors are selected from among the X types of common factors $Z_1(t)$ to $Z_X(t)$. At this time, M types of common factors may be selected in descending order of the variance $l_1(t)$ to $l_X(t)$, from among the X types of common factors $Z_1(t)$ to $Z_X(t)$.

In the first embodiment, the data processing apparatus 5 acquires user's biometric information from a separate measuring apparatus 100, analyzes the biometric information, and displays the analysis result. On the other hand, the functions of the data processing apparatus 5 may be incorporated in the measuring apparatus 100, and the data processing apparatus 5 and the measuring apparatus 100 may be configured as an integrated apparatus. Further, an aspect may be adopted in which the data processing apparatus 5 of the first embodiment and the data processing apparatus 5b of the second embodiment may be configured as a server through a communication network such as the Internet, and the user accesses and uses the server through the communication network.

The entire disclosure of Japanese Patent Application No. 2016-209167 is hereby incorporated herein by reference.

What is claimed is:

1. A data processing apparatus comprising:
a processor programmed to execute
a data acquiring step of acquiring sampling time series data including biometric information of any one of a heat flux, a wrist temperature, an oxygen saturation level in arterial blood, and a pulse rate;
a data aggregation step of aggregating N types (N≥3) of the sampling time series data to acquire M types (M≥2 and N>M) of classification time series data, wherein the data aggregation step includes
aggregating the N types of sampling data into X types (X M) of classification time series data,
executing principal component analysis or factor analysis of the N types of sampling data to execute the aggregation, and
selecting the M types from the X types of classification time series data as the M types having M largest magnitudes of variance of the classification time series data among the X types, wherein the M types of classification time series data include at least a first principle component and a second principle component, the first principle component representing metabolic intensity and the second principle component representing automatic nerve function degree;
a classification step of classifying the M types of classification time series data into a plurality of clusters; and
an appearance data generation step of generating time series appearance data for each cluster.

2. The data processing apparatus according to claim 1, wherein
the classification step includes plotting the M types of classification time series data in an M-dimensional space, and clustering the plots to classify the plots into the plurality of clusters.

3. The data processing apparatus according to claim 1, wherein
the appearance data generation step includes calculating an appearance probability at each calculation time of a plurality of calculation times by averaging the classification time series data belonging to the cluster with a predetermined time width while shifting through the calculation times.

4. The data processing apparatus according to claim 1, wherein
the processor is programmed to execute
a display control step of controlling display of the time series appearance data in a form of a dial with a time axis in a circumferential direction.

5. A data processing method comprising:
acquiring sampling time series data including biometric information of any one of a heat flux, a wrist temperature, an oxygen saturation level in arterial blood, and a pulse rate;
aggregating N types (N≥3) of the sampling time series data to acquire M types (M≥2 and N>M) of classification time series data, wherein the aggregating includes
aggregating the N types of sampling data into X types (X≥M) of classification time series data,
executing principal component analysis or factor analysis of the N types of sampling data to execute the aggregation, and
selecting the M types from the X types of classification time series data as the M types having M largest magnitudes of variance of the classification time series data among the X types, wherein the M types of classification time series data include at least a first principle component and a second principle component, the first principle component representing metabolic intensity and the second principle component representing automatic nerve function degree;

classifying the M types of classification time series data into a plurality of clusters; and generating time series appearance data for each cluster.

* * * * *